(12) United States Patent
Rosenblum

(10) Patent No.: US 6,529,801 B1
(45) Date of Patent: Mar. 4, 2003

(54) AUTOMATIC PRESCRIPTION DRUG DISPENSER

(75) Inventor: Ken Rosenblum, Mendota Heights, MN (US)

(73) Assignee: Mendota Healthcare, Inc., Minnetonka, MN (US)

( * ) Notice: Subject to any disclaimer, the term of this patent is extended or adjusted under 35 U.S.C. 154(b) by 0 days.

(21) Appl. No.: 09/714,802

(22) Filed: Nov. 16, 2000

Related U.S. Application Data

(60) Provisional application No. 60/210,303, filed on Jun. 8, 2000.

(51) Int. Cl.[7] ............................................. G06F 17/00
(52) U.S. Cl. ........................ 700/237; 700/232; 700/241
(58) Field of Search ................................ 700/231, 232, 700/236, 237, 241, 244; 705/2, 3

(56) References Cited

U.S. PATENT DOCUMENTS

| | | | |
|---|---|---|---|
| 5,713,485 A | | 2/1998 | Liff et al. ......................... 221/2 |
| 5,797,515 A | | 8/1998 | Liff et al. ......................... 221/2 |
| 5,907,493 A | * | 5/1999 | Boyer et al. .................. 700/213 |
| 6,026,375 A | * | 2/2000 | Hall et al. ..................... 701/201 |
| 6,039,251 A | * | 3/2000 | Holowko et al. ............. 235/375 |
| 6,046,761 A | * | 4/2000 | Echerer .................... 348/14.01 |
| 6,068,156 A | | 5/2000 | Liff et al. ......................... 221/7 |
| 6,202,923 B1 | * | 3/2001 | Boyer et al. .................. 235/375 |
| 6,283,322 B1 | | 9/2001 | Liff et al. ......................... 221/7 |
| 6,305,377 B1 | * | 10/2001 | Portwood et al. ............ 128/897 |
| 6,330,491 B1 | * | 12/2001 | Lion ............................. 700/232 |
| 6,411,567 B1 | * | 6/2002 | Niemiec et al. ............... 368/10 |

* cited by examiner

*Primary Examiner*—Khoi H. Tran
(74) *Attorney, Agent, or Firm*—Schwegman, Lundberg, Woessner & Kluth, P.A.

(57) ABSTRACT

An automatic prescription drug dispenser including a remote dispenser, a prescription entry system, and a communications network. The remote dispenser transmits and receives information from the communications network and dispenses prescription drugs to the patient. The prescription entry system transmits and receives information from the communications network and provides an input system for the doctor to electronically enter individual prescriptions for each patient. The communications network coordinates communications between the doctor, insurance carrier, and the remote dispenser. The remote dispenser stores, retrieves, and labels prescription drug and over-the-counter products directly to patients through a remote automated vending machine, a remote dispenser, a prescription entry system, and a communications network. The remote dispenser transmits and receives information from the communications network and dispenses prescription drugs to the patient. The prescription entry system transmits and receives information from the communications network and provides an input system for the doctor to electronically enter individual prescriptions for each patient. The communications network coordinates communications between the doctor, insurance carrier, and the remote dispenser.

2 Claims, 40 Drawing Sheets

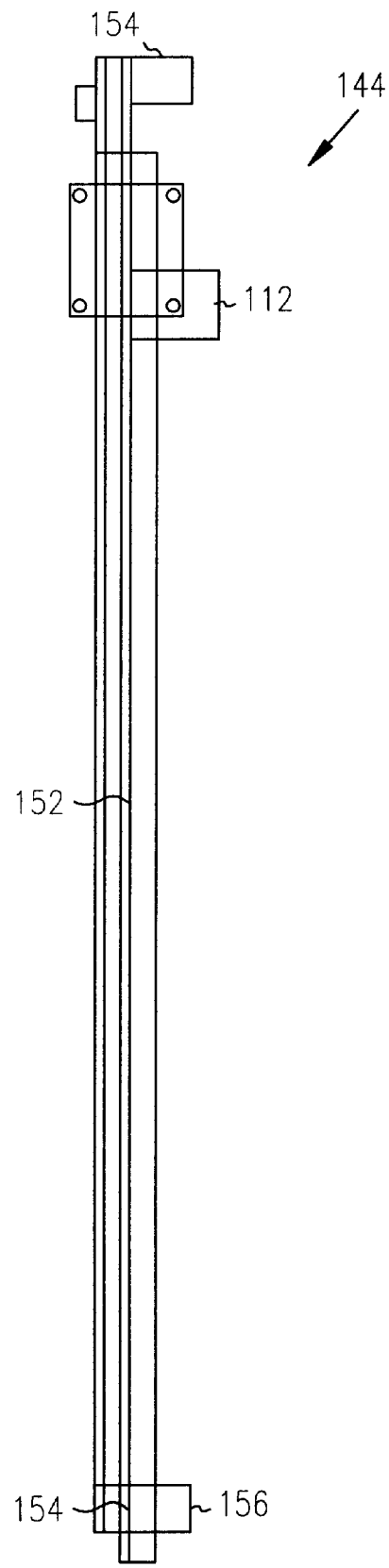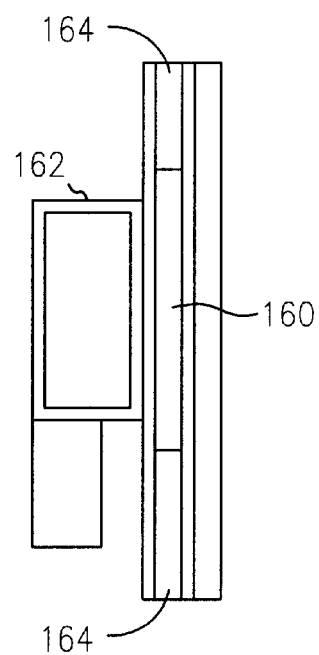
FIG. 17
FIG. 16

NEW PRESCRIPTION – CHOOSE SIG

- SCROLL UP OR DOWN AND PRESS ENTER TO PICK A COMMON SIG.
- PRESS ENTER ON THE DOTTED LINE TO MANUALLY ENTER A SIG.
- WHEN YOU BEGIN USING THE SYSTEM, NOTICE THAT COMMON SIGS ARE PROVIDED FOR YOU. IF YOU CHOOSE TO MAKE UP YOU OWN SIG, IT WILL BE ADDED TO YOUR LIST FOR THIS MED EACH TIME YOU PRESCRIBE THIS MED IN THE FUTURE.
- THE CURSOR WILL FIRST APPEAR ON THE LAST SIG YOU WROTE FOR THIS MED.

CHILDREN'S WEST      AUG. 12, 99
DR. S. KILEY              12:00 PM
NEW \ DONE \ REJECTED \ UTILITIES

JONATHAN PATIENTOWRITZ
20 YO MALE 50 kg. (1 OF 1)
AMPICILLIN 250mg CAPS   (D)

TAKE ONE CAP OID X 70               ~4300
TAKE TWO CAPS OID X 70
TAKE ONE CAP OID UNTIL GONE
TAKE TWO CAPS OID X 70
. . . . . . . . . . . .

TAB BETWEEN SCREENS — HOTSYNC
CANCEL OR GO BACK 1 FIELD | SCROLL UP AND DOWN | ENTER AND MOVE TO NEXT FIELD

FIG. 23E

NEW PRESCRIPTION – CREATE SIG 1

- SCROLL UP OR DOWN AND PRESS ENTER

- PRESS ENTER ON THE DOTTED LINE TO SPELL OUT A WORD THAT DOESN'T APPEAR.

- ONLY THOSE WORDS APPLICABLE TO THIS MED WILL APPEAR.

CHILDREN'S WEST      AUG. 12, 99
DR. S. KILEY              12:00 PM
NEW \ DONE \ REJECTED \ UTILITIES

JONATHAN PATIENTOWRITZ
20 YO MALE 50 kg. (1 OF 1)
AMPICILLIN 250mg CAPS   (D)

TAKE                                 ~4300
. . . . . .

TAB BETWEEN SCREENS — HOTSYNC
CANCEL OR GO BACK 1 FIELD | SCROLL UP AND DOWN | ENTER AND MOVE TO NEXT FIELD

NEW PRESCRIPTION – CREATE SIG 2

CHILDREN'S WEST    AUG. 12, 99
DR. S. KILEY              12:00 PM
NEW \ DONE \ REJECTED \ UTILITIES

JONATHAN PATIENTOWRITZ
20 YO MALE 50 kg. (1 OF 1)
AMPICILLIN 250mg CAPS   (D)

TAKE   1
       2
       . . .

~4300

- SCROLL UP OR DOWN AND PRESS ENTER
- PRESS ENTER ON THE DOTTED LINE TO SPELL OUT A WORD THAT DOESN'T APPEAR.
- ONLY THOSE WORDS APPLICABLE TO THIS MED WILL APPEAR.

TAB BETWEEN SCREENS | CANCEL OR GO BACK 1 FIELD | SCROLL UP AND DOWN | ENTER AND MOVE TO NEXT FIELD | HOTSYNC

FIG. 24C

NEW PRESCRIPTION – CREATE SIG 3

CHILDREN'S WEST    AUG. 12, 99
DR. S. KILEY              12:00 PM
NEW \ DONE \ REJECTED \ UTILITIES

JONATHAN PATIENTOWRITZ
20 YO MALE 50 kg. (1 OF 1)
AMPICILLIN 250mg CAPS   (D)

TAKE   CAPSULE
       TABLET
       . . . . . . . .

~4300

- SCROLL UP OR DOWN AND PRESS ENTER
- PRESS ENTER ON THE DOTTED LINE TO SPELL OUT A WORD THAT DOESN'T APPEAR.
- ONLY THOSE WORDS APPLICABLE TO THIS MED WILL APPEAR.

TAB BETWEEN SCREENS | CANCEL OR GO BACK 1 FIELD | SCROLL UP AND DOWN | ENTER AND MOVE TO NEXT FIELD | HOTSYNC

NEW PRESCRIPTION – CREATE SIG 4

- SCROLL UP OR DOWN AND PRESS ENTER
- PRESS ENTER ON THE DOTTED LINE TO SPELL OUT A WORD THAT DOESN'T APPEAR.
- ONLY THOSE WORDS APPLICABLE TO THIS MED WILL APPEAR.

CHILDREN'S WEST    AUG. 12, 99
DR. S. KILEY              12:00 PM
NEW \ DONE \ REJECTED \ UTILITIES

JONATHAN PATIENTOWRITZ
20 YO MALE 50 kg. (1 OF 1)
AMPICILLIN 250mg CAPS   (D)

TAKE 1 CAPSULE  [P O]  ~4300

TAB BETWEEN SCREENS    HOTSYNC
CANCEL OR GO BACK 1 FIELD | SCROLL UP AND DOWN | ENTER AND MOVE TO NEXT FIELD

FIG. 24D

NEW PRESCRIPTION – CREATE SIG 5

- SCROLL UP OR DOWN AND PRESS ENTER
- PRESS ENTER ON THE DOTTED LINE TO SPELL OUT A WORD THAT DOESN'T APPEAR.
- ONLY THOSE WORDS APPLICABLE TO THIS MED WILL APPEAR.

CHILDREN'S WEST    AUG. 12, 99
DR. S. KILEY              12:00 PM
NEW \ DONE \ REJECTED \ UTILITIES

JONATHAN PATIENTOWRITZ
20 YO MALE 50 kg. (1 OF 1)
AMPICILLIN 250mg CAPS   (D)

TAKE 1 CAPSULE PO  [OID / TID / Osh / Osh]  ~4300

TAB BETWEEN SCREENS    HOTSYNC
CANCEL OR GO BACK 1 FIELD | SCROLL UP AND DOWN | ENTER AND MOVE TO NEXT FIELD

NEW PRESCRIPTION – CREATE SIG 6

- SCROLL UP OR DOWN AND PRESS ENTER
- PRESS ENTER ON THE DOTTED LINE TO SPELL OUT A WORD THAT DOESN'T APPEAR.
- ONLY THOSE WORDS APPLICABLE TO THIS MED WILL APPEAR.

Device screen (4300):
- CHILDREN'S WEST    AUG. 12, 99
- DR. S. KILEY    12:00 PM
- NEW \ DONE \ REJECTED \ UTILITIES
- JONATHAN PATIENTOWRITZ
- 20 YO MALE 50 kg. (1 OF 1)
- AMPICILLIN 250mg CAPS (D)
- TAKE 1 CAPSULE PO OID
- UNTIL BOTTLE IS EMPTY
- FOR 7 DAYS
- FOR 10 DAYS
- FOR 14 DAYS Button labels: TAB BETWEEN SCREENS, HOTSYNC, CANCEL OR GO BACK 1 FIELD, SCROLL UP AND DOWN, ENTER AND MOVE TO NEXT FIELD

FIG. 25A

NEW PRESCRIPTION – ADD NEW SIG TO PERSONAL LIST?

- ENTER "YES" TO PLACE THIS NEW SIG ON YOUR "MY SIG" LIST.
  - WHEN A SIG ARE MANUALLY ENTERED SUCH AS THE ONE, IT WILL APPEAR ON YOUR PERSONALIZED "MY SIG" LIST FOR THIS MED. SIG INSTRUCTIONS CAN BE CONVENIENTLY PICKED FROM THE LIST WHENEVER YOU PRESCRIBE THIS DRUG. THE MOST RECENT SIG USED WILL APPEAR FIRST AND DEFAULT.
  - A MAXIMUM COMBINATION OF 5 PERSONAL OR STANDARD SIGS CAN BE ATTACHED TO EACH DRUG. IF AN ADDITIONAL SIG IS ENTERED. THE LAST SIG DROPS OFF FROM THE LIST.

Device screen (4300):
- CHILDREN'S WEST    AUG. 12, 99
- DR. S. KILEY    12:00 PM
- NEW \ DONE \ REJECTED \ UTILITIES
- JONATHAN PATIENTOWRITZ
- 20 YO MALE 50 kg. (1 OF 1)
- AMPICILLIN 250mg CAPS (D)
- TAKE 1 CAPSULE PO OID WITH MEALS UNTIL BOTTLE IS EMPTY.

Button labels: TAB BETWEEN SCREENS, HOTSYNC, CANCEL OR GO BACK 1 FIELD, SCROLL UP AND DOWN, ENTER AND MOVE TO NEXT FIELD

NEW PRESCRIPTION – CHOOSE # OF REFILLS AND DAW?

- SCROLL UP OR DOWN TO PICK THE NUMBER OF AUTHORIZED REFILL. THE DEFAULT IS ZERO
- SCROLL DOWN AND PRESS ENTER IF YOU WANT THE MEDICATION DAW (DISPENSED AS WRITTEN). THE DEFAULT IS "NO". IF DAW IS MARKED "YES", THE PRESCRIPTION LABEL WILL DISPLAY "DISPENSE AS WRITTEN".
- IF X REFILLS ARE AUTHORIZED AND THE MED IS DISPENSED FROM THE DISPENSER, A SCRIPT WILL ALSO PRINTOUT AUTHORIZING (X-1) REFILLS AND NOTING THAT AN ORIGINAL PRESCRIPTION WAS DISPENSED.

CHILDREN'S WEST    AUG. 12, 99
DR. S. KILEY       12:00 PM
NEW \ DONE \ REJECTED \ UTILITIES

JONATHAN PATIENTOWRITZ
20 YO MALE 50 kg. (1 OF 1)
AMPICILLIN 250mg CAPS   (D)

TAKE 1 CAPSULE PO OID WITH MEALS UNTIL BOTTLE IS EMPTY.

REFILLS [ 0 ]    DAW [ 11 ]

~4300

TAB BETWEEN SCREENS        HOTSYNC
CANCEL OR GO BACK 1 FIELD | SCROLL UP AND DOWN | ENTER AND MOVE TO NEXT FIELD

FIG. 25B

NEW PRESCRIPTION – PICK QUANTITY

- SCROLL DOWN AND PRESS ENTER TO SELECT A COMMON QUANTITY. AT FIRST, THESE QUANTITIES WILL BE THOSE COMMONLY WRITTEN FOR THIS MED. A "D" AFTER THE NUMBER INDICATES THAT THIS QUANTITY IS IN THE DISPENSER.
- IF YOU ENTER A TIME PERIOD IN WHICH TO TAKE THE MEDICATION (I.E. 7 DAYS), THE SYSTEM WILL CALCULATE THE CORRECT QUANTITY TO DISPENSE. THE CURSOR WILL AT FIRST BE ON THE NEXT LARGER QUANTITY IN THE DISPENSER, IF ANY.
- IF YOU ENTER A NEW QUANTITY, IT WILL APPEAR ON YOUR COMMON QUANTITY LIST FOR THIS MED. YOU CAN CHOOSE UP TO 6 COMMON QUANTITIES IF ANOTHER QUANTITY IS CHOSEN, THE LAST QUANTITY DROPS OFF THE LIST.
- PRESS ENTER ON THE DOTTED LINE TO PICK A DIFFERENT QUANTITY.

CHILDREN'S WEST    AUG. 12, 99
DR. S. KILEY       12:00 PM
NEW \ DONE \ REJECTED \ UTILITIES
JONATHAN PATIENTOWRITZ
20 YO MALE 50 kg. (1 OF 1)
AMPICILLIN 250mg CAPS   (D)
QUANTITY:     21 D
              28 D
              20
              30
              40
              . . .

REFILLS [ 0 ]    DAW [ 11 ]

~4300

TAB BETWEEN SCREENS        HOTSYNC
CANCEL OR GO BACK 1 FIELD | SCROLL UP AND DOWN | ENTER AND MOVE TO NEXT FIELD

FIG. 25C

NEW PRESCRIPTION – DIAL IN QUANTITY

- SCROLL UP OR DOWN TO CHANGE THE NUMBERS.
- SCROLL LEFT TO CHANGE A DIFFERENT DIGIT.
- PRESS ENTER WHEN FINISHED.

CHILDREN'S WEST    AUG. 12, 99
DR. S. KILEY    12:00 PM

NEW \ DONE \ REJECTED \ UTILITIES

JONATHAN PATIENTOWRITZ
20 YO MALE 50 kg. (1 OF 1)
AMPICILLIN 250mg CAPS (D)
QUANTITY: [ ][ ][2][8]

TAKE 1 CAPSULE PO QID WITH MEALS UNTIL BOTTLE IS EMPTY.

REFILLS [0]    DAW [11]

~4300

TAB BETWEEN SCREENS — HOTSYNC
CANCEL OR GO BACK 1 FIELD | SCROLL UP AND DOWN | ENTER AND MOVE TO NEXT FIELD

NEW PRESCRIPTION – WRITE ANOTHER FOR THIS PATIENT?

- PRESS ENTER IF THIS IS THE LAST PRESCRIPTION FOR THIS PATIENT.
- SCROLL DOWN AND PRESS ENTER IF YOU WISH TO WRITE ANOTHER PRESCRIPTION FOR THIS PATIENT.

CHILDREN'S WEST    AUG. 12, 99
DR. S. KILEY    12:00 PM

NEW \ DONE \ REJECTED \ UTILITIES

JONATHAN PATIENTOWRITZ
20 YO MALE 50 kg. (1 OF 1)
AMPICILLIN 250mg CAPS (D)
QUANTITY: 28

SAVE AND WRITE ANOTHER FOR THIS PATIENT

SAVE AND FINISH

CANCEL

~4300

TAB BETWEEN SCREENS — HOTSYNC
CANCEL OR GO BACK 1 FIELD | SCROLL UP AND DOWN | ENTER AND MOVE TO NEXT FIELD

FIG. 25E

NEW PRESCRIPTION - CHOOSE HOW TO DISPENSE

- HAVE PRESCRIPTION PRINTED OUT AT DISPENSING MACHINE IN WAITING ROOM..
- HAVE MEDICINE DISPENSED AT DISPENSER. PATIENT CAN CHANGE HIS MIND LATER.
- AUTOMATICALLY FAX OR E-MAIL PRESCRIPTION TO A PHARMACY.
- CANCEL PRESCRIPTION.
- (CURSOR DEFAULTS TO "DISPENSE AT DISPENSER:)

CHILDREN'S WEST    AUG. 12, 99
DR. S. KILEY            12:00 PM
NEW \ DONE \ REJECTED \ UTILITIES
JONATHAN PATIENTOWRITZ
20 YO MALE 50 kg. (1 OF 1)
AMPICILLIN 250mg CAPS  (D)
QUANTITY: 28 CAPSULES

PRINT PRESCRIPTION
(2 DRUGS IN DISPENSER)

FAX OR E-MAIL

CANCEL

~4300

TAB BETWEEN SCREENS — HOTSYNC
CANCEL OR GO BACK 1 FIELD | SCROLL UP AND DOWN | ENTER AND MOVE TO NEXT FIELD

FIG. 25F

NEW PRESCRIPTION - CHOOSE PHARMACY

- CHOOSE AN AREA PHARMACY WHERE THE PATIENT WISHES THE PRESCRIPTION FAXED OR E-MAILED.
- THE PATIENT SHOULD STILL RETRIEVE THE HARD COPY PRESCRIPTION FROM THE DISPENSING MACHINE TO BRING TO THE PHARMACY.
- THE ADVANTAGES OVER WRITING A PRESCRIPTION ARE:
  - HOPEFULLY, THE PATIENT WAIT AT THE PHARMACY WILL BE SHORTENED.
  - THE PHARMACIST WILL RECEIVE A TYPED PRESCRIPTION TOO ELIMINATE CHANCE OF MISREADING HANDWRITING.
- LOCAL PHARMACIST WILL BE ENTERED INTO THE DATABASE DURING INSTALLATION. CHANGES CAN BE MADE AT ANYTIME.

CHILDREN'S WEST    AUG. 12, 99
DR. S. KILEY            12:00 PM
NEW \ DONE \ REJECTED \ UTILITIES
JONATHAN PATIENTOWRITZ
20 YO MALE 50 kg. (1 OF 1)
AMPICILLIN 250mg CAPS  (D)
QUANTITY: 28 CAPSULES

WALLGREENS 1801 ROBER
CHILDREN'S 450 SMITH N
SNYDERS 800 OTTAWA ST
BUNDY A DRUG MALL DR
PLANET RX
DRUGSTORE.COM

~4300

TAB BETWEEN SCREENS — HOTSYNC
CANCEL OR GO BACK 1 FIELD | SCROLL UP AND DOWN | ENTER AND MOVE TO NEXT FIELD

FIG. 26A

VIEW WRITTEN PRESCRIPTIONS – REVISE OR DELETE?

- AT THIS POINT, THE PRESCRIPTION CAN BE EITHER:
  - REVISED
  - DELETED
- IN EITHER CASE,
  - THE DISPENSER WILL BE UPDATED AS TO THE DELETION OR REVISION
  - OR
  - A FAX OR E-MAIL WILL BE SENT TO THE PHARMACY NOTIFYING THEM OF THE CHANGE.
- THE SCREEN RETURNS TO THE LOOKUP SCREEN AT THE POINT FROM WHERE THIS PRESCRIPTION WAS PICKED.

CHILDREN'S WEST    AUG. 12, 99
DR. S. KILEY           12:00 PM
NEW / DONE \ REJECTED \ UTILITIES

JONATHAN PATIENTOWRITZ
20 YO MALE 50 kg. (1 OF 1)
AMPICILLIN 250mg CAPS   (D)
QUANTITY: 28 CAPSULES

REVISE THE PRESCRIPTION AND RESUBMIT.
DELETE THIS PRESCRIPTION AND REVISE INSURANCE INFORMATION.      ~4300

TAB BETWEEN SCREENS — HOTSYNC
CANCEL OR GO BACK 1 FIELD / SCROLL UP AND DOWN / ENTER AND MOVE TO NEXT FIELD

NEW REJECTED PRESCRIPTIONS – 1

- ALL TOO OFTEN INSURANCE CLAIMS WILL BE REJECTED BECAUSE A PRESCRIBED DRUG WAS NOT ON THE INSURANCE COMPANY'S FORMULARY.
- WHEN THIS HAPPENS THE FOLLOWING USUALLY OCCURS:
  - THE PHARMACIST CALLS THE DOCTORS OFFICE AND ASKS FOR A NURSE. HE IS PUT ON HOLD.
  - THE NURSE LISTENS TO THE PRESCRIPTION PROBLEM AND TELLS THE PHARMACIST SHE WILL CALL HIM BACK AFTER SHE ASKS THE DOCTOR FOR A DRUG CHANGE.
  - BETWEEN PATIENT'S THE NURSE ASKS THE DOCTOR FOR AND PUTS IN OK FOR THE DRUG CHANGE.
  - THE NURSE CALLS BACK THE PHARMACIST AND IS PUT ON HOLD.
  - THE NURSE RELAYS THE PRESCRIPTION CHANGE TO THE PHARMACIST.
- NOW, THESE ISSUES CAN BE HANDLED IMMEDIATELY BY THE PRESCRIBER BY PUSHING A FEW BUTTONS ON THE PALM PILOT.

CHILDREN'S WEST    AUG. 12, 99
DR. S. KILEY           12:00 PM
NEW \ DONE / REJECTED \ UTILITIES

PATIENTOWRITZ, JONATHAN   40y
12-28 7:30 PM AMPICLIN
DRUG NOT ON FORMULARY
(BLUE CROSS AWARE GOLD)

JOHNSON, MAYBELLE         5m
12-28 2:20 PM PERCENT
QUANTITY TOO LARGE (MEDICARE)     ~4300

TAB BETWEEN SCREENS — HOTSYNC
CANCEL OR GO BACK 1 FIELD / SCROLL UP AND DOWN / ENTER AND MOVE TO NEXT FIELD

FIG. 27A

NEW PEDIATRIC PRESCRIPTION – CHOOSE PATIENT

- PATIENT NAMES AND AGES ARE DISPLAYED ON THIS SCREEN. IF THE PATIENT IS UNDER 3 YEARS OLD, THE AGE WILL APPEAR IN MONTHS.
- SCROLL DOWN AND PRESS ENTER TO SELECT A PATIENT.
- AT THE BOTTOM OF THE SCREEN, SCROLLING BEGINS 1 SCREEN AT A TIME.
- AT THE FIRST CHANGE OF DIRECTION, SCROLLING WILL OCCUR 1 RECORD AT A TIME.
- WHEN YOU REACH THE TOP OR BOTTOM OF SCREEN, SCROLLING WILL AGAIN OCCUR 1 SCREEN AT A TIME.
- IF YOU CAN NOT FIND THE PATIENT'S NAME, PRESS ENTER ON THE DOTTED LINE TO ENTER A PATIENT'S NAME BY TYPING ON THE KEYBOARD THAT APPEARS.

```
CHILDREN'S WEST     AUG. 12, 99
DR. S. KILEY             12:00 PM
NEW \ DONE \ REJECTED \ UTILITIES

PATIENTOWRITZ, JONATHAN   40yM
JOHNSON, MAYBELLE         5yf
CLINTON, WILLIAM          6mM
HIPPEORATES, SAM          68yM
PATIENTOWRITZ, JONATHAN   40yM
JOHNSON, MAYBELLE         5yf
CLINTON, WILLIAM          6mM
HIPPEORATES, SAM          68yM
JOHNSON, MAYBELLE         5yf
. . . . . . . . . . .
```

~4300

TAB BETWEEN SCREENS — HOTSYNC
CANCEL OR GO BACK 1 FIELD | SCROLL UP AND DOWN | ENTER AND MOVE TO NEXT FIELD

NEW PEDIATRIC PRESCRIPTION – FIND DRUG

- CHOOSE WHETHER TO DISPLAY ALL PERSONAL MEDS LIST OR ALL MEDS. DEFAULT IS "MY MEDS".
- SCROLL UP OR DOWN TO THE 1ST 2 LETTERS OF THE MEDICATION AND PRESS ENTER.
- FOR THE "ALL MEDS" LIST, YOU WILL BE PROMPTED (IDENTICAL TO THIS SCREEN) FOR THE SECOND LETTER IN THE DRUG NAME.
- BOTH BRAND AND GENERIC NAMES ARE ON THE LIST.
- NEXT, A LIST WILL APPEAR OF THE 1ST 4 LETTERS OF THE DRUG NAME. PICK A DRUG NAME AS YOU DID ABOVE.

```
CHILDREN'S WEST     AUG. 12, 99
DR. S. KILEY             12:00 PM
NEW \ DONE \ REJECTED \ UTILITIES
AB        JUDY HORNER
CD        4 YO FEMALE
EF        15 kg. (1 FO 1)
GH
IJK       [ MY PATIENTS ]
LM
NO        [ ALL PATIENTS ]
PQR
ST
UV
WXYZ
```

~4300

TAB BETWEEN SCREENS — HOTSYNC
CANCEL OR GO BACK 1 FIELD | SCROLL UP AND DOWN | ENTER AND MOVE TO NEXT FIELD

FIG. 28E

NEW PEDIATRIC PRESCRIPTION – CHOOSE DRUG

- SCROLL DOWN AND PRESS ENTER TO SELECT A MEDICATION.
- AT THE BOTTOM OF THE SCREEN, SCROLLING BEGINS 1 SCREEN AT A TIME.
- AT THE FIRST CHANGE OF DIRECTION, SCROLLING WILL OCCUR 1 RECORD AT A TIME.
- WHEN YOU REACH THE TOP OR BOTTOM OF SCREEN, SCROLLING WILL AGAIN OCCUR 1 SCREEN AT A TIME.
- THE LETTER 'D' AT THE END OF THE LINE SIGNIFIES THAT THE DRUG IS IN THE DISPENSER
- IF THE DRUG IS CHOSEN FROM THE EXTENSIVE "ALL MEDS" LIST IN FROM THE PDR, YOU WILL BE ASKED IF YOU WISH TO MOVE THIS DRUG TO YOUR MUCH SHORTER "MY MEDS" LIST.
- IF THE DRUG HAS MORE THAN ONE DOSAGE FORM OR STRENGTH, A LIST OF DOSAGES AND STRENGTHS WILL APPEAR TO PICK FROM.

Device screen shows:
CHILDREN'S WEST   AUG. 12, 99
DR. S. KILEY          12:00 PM
NEW \ DONE \ REJECTED \ UTILITIES
JUDY HORNER ALLLLLLLLLLLLLLLL    D
ALLLLLLLLLLLLLLL     D
ALLLLLLLLLLLLLLL
ALLLLLLLLLLLLLLLL    D
ALLLLLLLLLLLLLLLL    D
ALLLLLLLLLLLLLLLL
ALLLLLLLLLLLLLLLL    D
ALLLLLLLLLLLLLLLL
ALLLLL XXXXXXXXXXX   D Buttons: TAB BETWEEN SCREENS, CANCEL OR GO BACK 1 FIELD, SCROLL UP AND DOWN, ENTER AND MOVE TO NEXT FIELD, HOTSYNC — 4300

NEW PEDIATRIC PRESCRIPTION – CHOOSE SIG

- SCROLL UP OR DOWN AND PRESS ENTER TO PICK A COMMON SIG.
- PRESS ENTER ON THE DOTTED LINE TO MANUALLY ENTER A SIG.
- WHEN YOU BEGIN USING THE SYSTEM, NOTICE THAT COMMON SIGS ARE PROVIDED FOR YOU. IF YOU CHOOSE TO MAKE UP YOU OWN SIG, IT WILL BE ADDED TO YOUR LIST FOR THIS MED EACH TIME YOU PRESCRIBE THIS MED IN THE FUTURE.
- THE CURSOR WILL FIRST APPEAR ON THE LAST SIG YOU WROTE FOR THIS MED.

Device screen shows:
CHILDREN'S WEST   AUG. 12, 99
DR. S. KILEY          12:00 PM
NEW \ DONE \ REJECTED \ UTILITIES JUDY HORNER
4 YO FEMALE 15 kg. (1 OF 1)
AMPICILLIN 250mg/5ML SUPP (D)

TAKE 75 m/k/d (tsp) OID x 70
TAKE 100 m/k/d (ml) OID x 70
TAKE 75 mg/kg/d (ml) OID x 70
TAKE 100 mg/kg/d (tsp)
OID x 100
. . . . . . . . . . .

Buttons: TAB BETWEEN SCREENS, CANCEL OR GO BACK 1 FIELD, SCROLL UP AND DOWN, ENTER AND MOVE TO NEXT FIELD, HOTSYNC — 4300

FIG. 29A

NEW PEDIATRIC PRESCRIPTION – CHOOSE # OF REFILLS AND DAW?

- SCROLL UP OR DOWN TO PICK THE NUMBER OF AUTHORIZED REFILL. THE DEFAULT IS ZERO
- IF X REFILLS ARE AUTHORIZED AND THE PRESCRIPTION IS DISPENSED FROM THE DISPENSER, A PAPER SUBSCRIPTION WILL PRINT AUTHORIZING (X-1) REFILLS AND IT WILL BE NOTED THAT THE ORIGINAL WAS DISPENSED FROM THE DISPENSER.
- SCROLL DOWN AND PRESS ENTER IF YOU WANT THE MEDICATION DAW (DISPENSED AS WRITTEN). THE DEFAULT IS "NO".

Device screen (4300):
CHILDREN'S WEST   AUG. 12, 99
DR. S. KILEY      12:00 PM
NEW \ DONE \ REJECTED \ UTILITIES
JUDY HORNER
5 YO FEMALE 15 kg. (1 OF 1)
AMPICILLIN 250mg/SML SUPP (D)

TAKE 1-1/4 TEASPOONS FOUR TIMES A DAY FOR 7 DAYS

REFILLS [0]   DAW [11]

TAB BETWEEN SCREENS — HOTSYNC
CANCEL OR GO BACK 1 FIELD | SCROLL UP AND DOWN | ENTER AND MOVE TO NEXT FIELD

FIG. 29B

NEW PEDIATRIC PRESCRIPTION – PICK QUANTITY

- THE PROPER TOTAL DRUG AMOUNT WILL BE CALCULATED. SCROLL DOWN AND PRESS ENTER TO SELECT A STANDARD OR PERSONAL QUANTITY FOR THIS MED. A "D" AFTER THE NUMBER INDICATES THAT THIS QUANTITY IS IN THE DISPENSER.
- THE CORRECT AMOUNT WILL BE CALCULATED AND THE CURSOR WILL BE ON THIS SIZED CONTAINER, OR THE NEXT LARGER SIZED CONTAINER IN THE DISPENSER.
- IF YOU PICK A LARGER AMOUNT THAN IS AVAILABLE. 2 BOTTLES MAY BE DISPENSED.
- PRESS ENTER ON THE DOTTED LINE TO PICK A DIFFERENT QUANTITY.

Device screen (4300):
CHILDREN'S WEST   AUG. 12, 99
DR. S. KILEY      12:00 PM
NEW \ DONE \ REJECTED \ UTILITIES
JUDY HORNER
4 YO FEMALE 15 kg. (1 OF 1)
AMPICILLIN 250mg/SML SUPP (D)
QUANTITY:
  80  D
  100 D
  150 D
  230 D
  250 D
  300 D
  ...

TAB BETWEEN SCREENS — HOTSYNC
CANCEL OR GO BACK 1 FIELD | SCROLL UP AND DOWN | ENTER AND MOVE TO NEXT FIELD

FIG. 29C

NEW PRESCRIPTION – WRITE ANOTHER FOR THIS PATIENT?

- PRESS ENTER IF THIS IS THE LAST PRESCRIPTION FOR THIS PATIENT.
- SCROLL DOWN AND PRESS ENTER IF YOU WISH TO WRITE ANOTHER PRESCRIPTION FOR THIS PATIENT.

CHILDREN'S WEST   AUG. 12, 99
DR. S. KILEY        12:00 PM
NEW \ DONE \ REJECTED \ UTILITIES
JONATHAN PATIENTOWRITZ
20 YO MALE 50 kg. (1 OF 1)
AMPICILLIN 250mg CAPS (D)
QUANTITY: 28

SAVE AND WRITE ANOTHER FOR THIS PATIENT

SAVE AND FINISH

CANCEL

~4300

TAB BETWEEN SCREENS        HOTSYNC
CANCEL OR GO BACK 1 FIELD   SCROLL UP AND DOWN   ENTER AND MOVE TO NEXT FIELD

NEW PRESCRIPTION – CHOOSE HOW TO DISPENSE

- HAVE PRESCRIPTION PRINTED OUT AT DISPENSING MACHINE IN WAITING ROOM..
- HAVE MEDICINE DISPENSED AT DISPENSER. PATIENT CAN CHANGE HIS MIND LATER.
- AUTOMATICALLY FAX OR E-MAIL PRESCRIPTION TO A PHARMACY.
- CANCEL PRESCRIPTION.
- (CURSOR DEFAULTS TO "DISPENSE AT DISPENSER:")

CHILDREN'S WEST   AUG. 12, 99
DR. S. KILEY        12:00 PM
NEW \ DONE \ REJECTED \ UTILITIES
JONATHAN PATIENTOWRITZ
20 YO MALE 50 kg. (1 OF 1)
AMPICILLIN 250mg CAPS (D)
QUANTITY: 28 CAPSULES

PRINT PRESCRIPTION (2)
(2 DRUGS IN DISPENSER)

FAX OR E-MAIL

CANCEL

~4300

TAB BETWEEN SCREENS        HOTSYNC
CANCEL OR GO BACK 1 FIELD   SCROLL UP AND DOWN   ENTER AND MOVE TO NEXT FIELD

FIG. 29E

NEW PRESCRIPTION – CHOOSE PHARMACY

- CHOOSE AN AREA PHARMACY WHERE THE PATIENT WISHES THE PRESCRIPTION FAXED OR E-MAILED.
- THE PATIENT SHOULD STILL RETRIEVE THE HARD COPY PRESCRIPTION FROM THE DISPENSING MACHINE TO BRING TO THE PHARMACY.
- THE ADVANTAGES OVER WRITING A PRESCRIPTION ARE:
  - HOPEFULLY, THE PATIENT WAIT AT THE PHARMACY WILL BE SHORTENED.
  - THE PHARMACIST WILL RECEIVE A TYPED PRESCRIPTION TOO ELIMINATE CHANCE OF MISREADING HANDWRITING.
- LOCAL PHARMACIST WILL BE ENTERED INTO THE DATABASE DURING INSTALLATION. CHANGES CAN BE MADE AT ANYTIME.

CHILDREN'S WEST   AUG. 12, 99
DR. S. KILEY         12:00 PM
NEW \ DONE \ REJECTED \ UTILITIES
JONATHAN PATIENTOWRITZ
20 YO MALE 50 kg. (1 OF 1)
AMPICILLIN 250mg CAPS  (D)
QUANTITY: 28 CAPSULES

WALLGREENS 1801 ROBER
CHILDREN'S 450 SMITH N
SNYDERS 800 OTTAWA ST
BUNDY A DRUG MALL DR
PLANET RX
DRUGSTORE.COM

TAB BETWEEN SCREENS   HOTSYNC
CANCEL OR GO BACK 1 FIELD   SCROLL UP AND DOWN   ENTER AND MOVE TO NEXT FIELD

FIG. 29F

NEW PEDIATRIC PRESCRIPTION – CONFIRMATION OF SCRIPT

- THIS POPUP WINDOW VERIFIES THAT THE PRESCRIPTION HAS BEEN SAVED. IT DISAPPEARS AFTER 2 SECONDS.
- WHEN PRESCRIPTIONS ARE WAITING TO BE TRANSMITTED, THE CLINIC NAME WILL BE SHADED AT THE TOP OF THE SCREEN.

CHILDREN'S WEST   AUG. 12, 99
DR. S. KILEY         12:00 PM
NEW \ DONE \ REJECTED \ UTILITIES
JONATHAN PATIENTOWRITZ
20 YO MALE 50 kg. (1 OF 1)
AMPICILLIN 250mg CAPS  (D)
QUANTITY: 28 CAPSULES

ONE PRESCRIPTION FOR JONATHAN PATIENTOWRITZ HAS BEEN SAVED. PLEASE UPLOAD THE INFORMATION.

FIG. 30

AUTOMATIC PRESCRIPTION DRUG DISPENSER

PRIORITY OF INVENTION

This application claims priority of invention under 35 U.S.C. §119(e) from U.S. Provisional Application No. 60/210,303 filed Jun. 8, 2000.

TECHNICAL FIELD

The present invention concerns dispensing systems, such as vending machines, particularly dispensing systems for prescription drugs.

BACKGROUND OF THE INVENTION

Travelling from place to place and waiting for a prescription to be filled when sick or while accompanying a sick family member has been an unpleasant experience for many. The typical journey includes a visit with a doctor at a clinic, waiting for the doctor to scribble a handwritten prescription, travelling to a pharmacy, giving the pharmacist the handwritten prescription, and waiting for the pharmacist to interpret and fill the prescription. Many times if the handwritten prescription is difficult to read, the pharmacist will need to call the doctor to confirm the prescription. In addition, many times the patient's insurance carrier will not cover the particular prescription because the particular drug is not on the insurance carrier's present formulary or because the quantity exceeds the insurance carrier's coverage limits. These insurance problems may require contacting the insurance carrier, the doctor to rewrite the prescription, or both. Meanwhile, the already ill and tired patient is required to wait as the doctor, pharmacist, and insurance carrier sort out and deliver the prescription to the patient, before they may go home for needed rest.

There are several problems with the present prescription drug delivery system. First, existing systems are slow and require the patient to travel from place to place or wait as overworked pharmacists try to quickly and correctly fill prescriptions for numerous irritable patients. In addition to being slow, the system is prone to human error.

In addition, the present system lacks coordination between the doctor, pharmacists and insurance carrier, sometimes requiring unwanted revisits to the doctor's office or calls between the doctor, pharmacist, and insurance carrier.

Accordingly, there is a need for a prescription drug delivery system that quickly and efficiently delivers the prescription drug to the patient at a convenient location such as the doctor's office and coordinates communications between the doctor, pharmacist, and insurance carrier.

SUMMARY OF INVENTION

To address these needs, the inventor devised a new drug delivery system. One exemplary system consists of a remote dispenser, a prescription entry system, and a communications network. The remote dispenser transmits and receives information from the communications network and dispenses prescription drugs to the patient. The prescription entry system transmits and receives information from the communications network and provides an input system for the doctor to electronically enter individual prescriptions for each patient. The communications network coordinates communications between the doctor, insurance carrier, and the remote dispenser.

BRIEF DESCRIPTION OF DRAWINGS

FIG. 16 is a front view of one embodiment of the y-axis system of the gantry transport system of the present invention.

FIG. 17 is a cross sectional view of the y-axis system of the present invention.

FIGS. 23–30 are screen views of one embodiment of a prescription entry system for a handheld computing device of the present invention.

DETAILED DESCRIPTION OF PREFERRED EMBODIMENTS

The following detailed description, which references and incorporates the Figures, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

The automatic prescription dispensing system provides safe, convenient and immediate prescription drug service to patients in primary, urgent, acute, and emergency care settings. The system provides several advantages including, but not limited to, entry of a prescription into a handheld computer using a unique software application, downloading of prescription and patient data from a central server database, acceptance of credit, debit, smart and ATM cards or cash, automatic verification by barcode of each drug package for correct drug and expiration date before dispensing, optional prescription print-out instead of dispensing the prescription drugs, dispensing of appropriate drug education information and payment receipts, transfer of information to and from a central server database regarding available product information, restocking, product returns, prescription-filled and prescription-printed flags, patient requests for automatic refills and refill reminders, and failure information, and alert the central server if security of the dispensing system is compromised.

System Architecture

Figure 1:
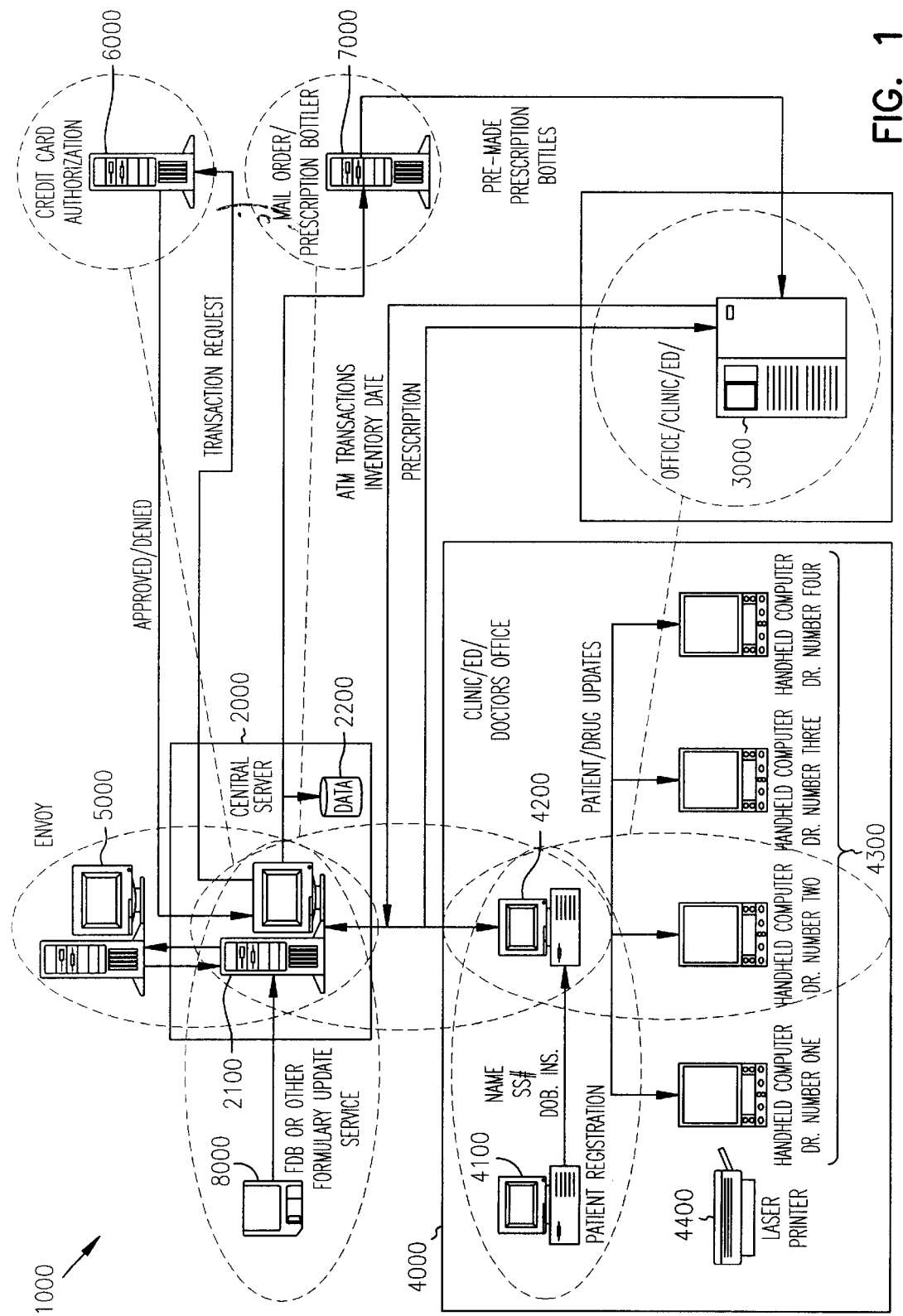
FIG. 1 is a schematic diagram of a high-level computer system architecture embodiment of the invention.

FIG. 1 is a schematic diagram of a high-level computer system architecture embodiment of the invention. The system 1000 is a distributed network comprising a central server 2000, a remote dispenser 3000, and one or more clinic systems 4000. A medical patient who visits a physician at a clinic where a clinic system 4000 is located receives a prescription that is filled at the remote dispenser 3000 if the prescription is so authorized, or adjudicated, by central server 2000. To decide whether to authorize the prescription, central server 2000 is in distributed network communications with the adjudication system 5000, credit card authorization system 6000, mail order/prescription bottler system 7000, and formulary update service 8000.

Central Server

Central server 2000 captures all data that is created by the various other components of the system 1000. It also prepares, sends, and receives all adjudicated claims; prepares, sends, and receives all credit card payments; and retains inventory data for all remote dispensers.

An example of the hardware and software that are suitable for the central server 2000 is a Compaq Prolient 1800 computer system 2100 that is expandable to dual processors, one gigabyte of SDRAM central memory, and 250 gigabytes of SCSI hard drive storage 2200; Microsoft Windows NT Server 4.0 operating system; and Microsoft SQL Server 7.0 database. Other generally equivalently performing hardware and software could be substituted in a known manner without limiting the scope of the invention. In accordance with known principles, the design of the system should be such that the system functions are not dependent upon the particular hardware or software selected for implementation, thus permitting the system to migrate to other hardware or software platforms without any change in the scope of the invention.

A software application running on the central server 2000 is responsible for setting up authorized clinic systems 4000 and prescribers of prescriptions. This application is preferably written in Java for display in an Internet browser application running on a client of the central server 2000 or a clinic system 4000 (assuming appropriate authorization criteria are met).

Another software application running on the central server 2000 is responsible for generating reports to document the operation and performance of system 1000 in accordance with well-known principles. Reports are preferably created on central server 2000 and sent to a printer anyplace on the network for generation of hard copy. A commercially available report generation system, preferably but not necessarily Crystal Reports, may be used to format the report data in accordance with well-known principles.

Another software application running on the central server 2000 is responsible for processing transactions associated with the adjudication of valid prescriptions. A commercially available adjudication application, preferably but not necessarily Claims Engine 2000, may be used in accordance with well-known principles to exchange data between central server 2000 and adjudication system 5000.

Another software application running on the central server 2000 is responsible for packaging, sending and receiving credit card payment and reversal transactions generated by patients who must pay for the prescriptions they receive. A commercially available but proprietary authorization application, provided by the credit card vendor (s), may be used in accordance with well-known principles to exchange data between central server 2000 and credit card authorization server 6000.

Another software application running on the central server 2000 is responsible for monitoring the inventory levels of the various products dispensed from each of the remote dispensers 3000. In accordance with known principles, monitored inventory levels are used to determine reorder points (times and quantities) for the products. This application also determines which National Drug Code (NDC) is used to adjudicate the prescription when a particular product is prescribed. The application is preferably written in Java for display in an Internet browser application. The application will run both on the central server 2000 and on the clinic workstation 4200. Optionally, inventory levels are monitored by the remote dispenser 3000. The central server 2000 provides vendor and product information and the remote dispenser 3000 would interact with the vendors and perform the inventory control functions. Summary reports are uploaded to the central server 3000.

Another software application running on the central server 2000 is responsible for importing and maintaining the formulary. The preferred method is to import and maintain formulary data files 8000 provided by First Databank (FDB), using an application written in Java and using the FDB toolkit provided by the vendor.

Another software application running on the central server 2000 is responsible for setting the price of products dispensed from remote dispenser 3000. The preferred embodiment is a program written in Java.

Remote Dispenser

Figure 2:
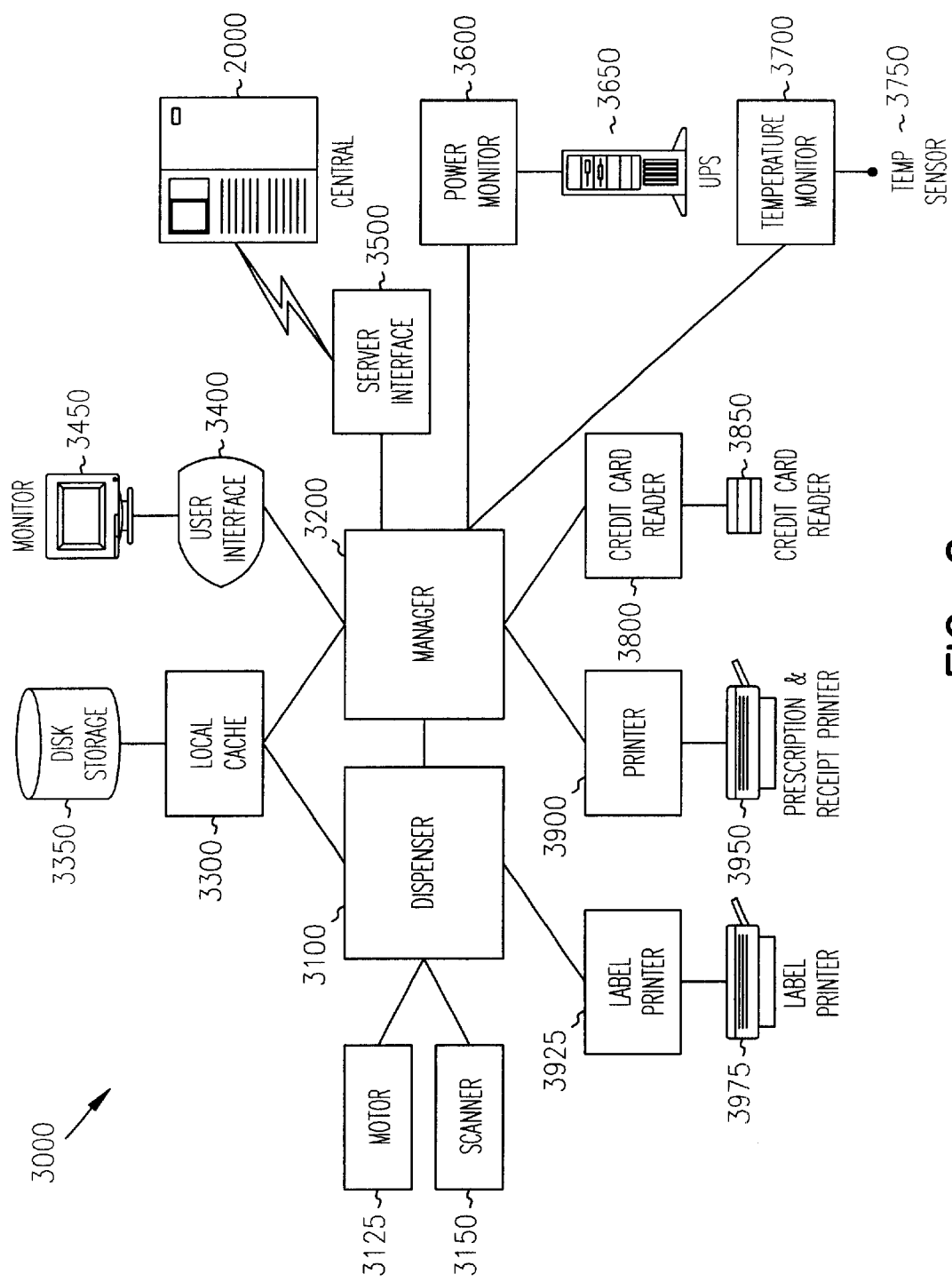
FIG. 2 is a schematic diagram of a software architecture embodiment of the remote dispenser of the present invention.

FIG. 2 is a schematic diagram of the software architecture of the remote dispenser 3000. From a software standpoint, remote dispenser 3000 comprises two major subcomponents, dispenser module 3100 and manager module 3200, which communicate with each other in any well-known manner. Dispenser module 3100 controls the actual dispensing of the product from the remote dispenser 3000. Given properly verified data, dispenser module 3100 will dispense properly labeled product. To do so, it issues appropriate commands to motor 3125, scanner 3150 and label printer driver 3925 based on communications with manager module 3200 and local cache 3300.

Manager module 3200 is the main controller of remote dispenser 3000. It coordinates and controls the interaction between all of the other hardware and software components of the remote dispenser 3000. It communicates with dispenser module 3100, local cache 3300, user interface 3400, server interface 3500, power monitor 3600, temperature monitor 3700, cash handler or debit, ATM, smart, or credit card reader driver 3800, and prescription/receipt printer driver 3900.

Local cache 3300 is responsible for storing and retrieving data in local storage 3350. The local cache 3300 manages data related to product inventory, system configuration, and advertising. It communicates with dispenser module 3100 and manager module 3200 as required. Local storage 3350 is any appropriate data storage device performing typical data storage and handling in a well-known manner.

User interface 3400 is responsible for interacting with patients and maintenance personnel. It controls the screen display shown on visual monitor 3450, and also manages timeouts that can be encountered at each step of the process of using remote dispenser 3000.

Server interface 3500 is responsible for communications with the central server 2000. It will send and receive data between the remote dispenser 3000 and the central server 2000. It is also responsible for translating data to and from formats required by the remote dispenser 3000 and central server 2000.

Power monitor 3600 monitors the normal line voltage power supply to remote dispenser 3000 and activates uninterruptible power supply (UPS) 3650 as required.

Temperature monitor 3700 monitors the ambient temperature inside remote dispenser 3000 with a temperature sensor 3750.

Card reader driver 3800 allows manager module 3200 to operate a commercially available cash handler, ATM, smart debit or credit card reader 3850 in a well-known manner.

Prescription/receipt printer driver 3900 allows manager module 3200 to operate a prescription/receipt printer 3950 in a well-known manner.

Label printer driver 3925 allows dispenser module 3100 to operate a label printer 3975 in a well-known manner.

Manager

The manager module 3200 comprises various other software modules to support the following activities at the remote dispenser 3000.

Dispensing of Products

A patient who has a valid prescription voucher from a physician initiates the dispensing activity at visual monitor 3450. The patient inputs the voucher number, patient birth date, their selection of products (if any beyond those included in the prescription), and a credit, debit, ATM, or smart card number through use of card reader 3850. Manager module 3200 communicates with central server 2000 to authorize the entire transaction. Once authorized, manager module 3200 communicates with dispenser module 3100 to generate the dispensed medications; and with prescription/receipt printer driver 3900 to print appropriate information and receipts on prescription/receipt printer 3950. The patient receives drug specific education advertising via DVD while product is being received. The patient is asked if they would like additional information about their medication sent to them, such as reminders about refilling their prescriptions. In addition, a toll free pharmacist helpline is offered via the interface.

Restocking of Products

A clinic staff person, for example, initiates the restocking activity. This person would typically be a local person at the clinic at which remote dispenser 3000 is located. Restocking involves removing magazines that are empty or that have been selected for removal (e.g., expired or superceded products). Manager module 3200 tracks restocking activity and communicates appropriate data over server interface 3500 to central server 2000 so that proper inventory control is maintained.

Diagnostics

A maintenance person initiates the diagnostic activity. This person would typically be a dedicated maintenance person who travels from one remote dispenser 3000 to the next. Diagnostics include testing the availability and functionality of the hardware components of remote dispenser 3000. In addition to testing individual components, the entire dispensing activity can be tested by dispensing a placebo product.

The maintenance and diagnostic routines are preferably implemented by putting an invisible button on the voucher number entry screen portion of visual monitor 3450. For example, after entering a special password code for voucher number, and pressing the hidden button twice, the maintenance mode is entered if the special password code is otherwise valid. A selection of available options, depending on authorization level, is displayed: restocking of products, rescanning of product magazines to verify inventory; display of current inventory (including an option to print the result on prescription/receipt printer 3950); diagnostic routines; communication status (e.g., "pinging" other devices to ensure that communications links are active); dispensing a placebo product to display the status of the dispensing operation by exercising all devices including motors, scanners, and printers (the placebo product will be labeled to test label printer 3975); manual operation of available hardware (e.g., activating various motors, displaying scanned input from a test of input devices, and the like); confirmation of configuration for devices that are configurable (e.g., communications port parameters, logical addresses of each device); and, status of communications to central server 2000 (typically a multi-step routine in which first visual monitor 3450 displays the status of the connection to central server 2000, followed by an active pinging of central server 2000, followed by pinging of any router that may be between server interface 3500 and central server 2000, etc.).

Advertising and/or Educational Information

Visual monitor 3450 may display information such as educational information or advertisements during idle times and during certain stages of the dispensing activity. The educational information or advertisements may be in the form of images, animation, audiovisual works, etc. without limiting the scope of the invention.

Error Recovery

Manager module 3200 will attempt to recover from errors that are encountered during dispensing. Such errors include communication problems with the central server 2000, and hardware problems on the remote dispenser 3000. The central server 2000 will be appropriately notified of the errors.

Monitoring

Manager module 3200 notifies central server 2000 when appropriate boundary conditions are approached or exceeded. Such conditions include temperature, interruption to normal line voltage power supply, paper supply for each printer 3950 and 3975, and physical access to remote dispenser 3000.

Clinic System

Each clinic system 4000 comprises a patient registration client 4100, a clinic workstation 4200, one or more handheld computers 4300 (as an example only, FIG. 1 shows four such handheld computers 4300), and one or more laser printers 4400. Registration client 4100 may be any suitably configured network capable personal computer or dedicated terminal in communication with clinic workstation 4200. Clinic workstation 4200 may be any suitably configured network capable personal computer; the preferred configuration is a small form factor personal computer from Compaq, running Microsoft Windows NT Workstation 4.0. Handheld computer(s) 4300 may be any suitably configured portable computers such as a laptop, palmtop, personal digital assistant, etc. The preferred model is a Palm Vx from Palm Computing, running Palm OS. Laser printer 4400 is connected to the clinic system 4000 in a well-known manner and may be any suitably configured model of laser printer.

A software application for client registration runs on the clinic workstation 4200, and is written in a language pertinent to that platform, preferably Java for display in an Internet browser application running on the patient registration client 4100.

A software application for prescription writing runs on both the handheld computers 4300 and the clinic workstation 4200, and is written in languages pertinent to each platform. The software application processes the creation of prescriptions and vouchers that may be used to obtain prescriptions from the remote dispenser 3000; printing of prescriptions, vouchers, and adjudication results; and modifications to prescriptions and vouchers. The portion of the software that runs on the handheld computers 4300 is preferably an application for the Palm OS developed with the CodeWarrior development platform, but this is not a limitation on the scope of the invention. The portion of the software that runs on the clinic workstation 4200 is preferably a Java application for display in an Internet browser application running on the workstation 4200, but this also is not a limitation on the scope of the invention.

Each clinic system 4000 is connected to the central server 2000 through well-known networking techniques, such as a frame relay cloud or a virtual private network (VPN) or both.

Adjudication System

The adjudication system 5000 communicates with third party payers through a "switch" company such as Envoy or NDC. A commercially available application, provided by the PBM, may be used in accordance with well-known principles to exchange data between central server 2000 and adjudication system 5000.

Credit, Debit, ATM, or Smart Card Authorization System

The card authorization system 6000 is under the control of a third-party credit card transaction clearing house. As noted above, custom written software is used to exchange data between central server 2000 and credit card authorization system 6000.

Mail Order/Prescription Bottler System

The mail order/prescription bottler system 7000 is under the control of a third-party distributor of products to be provided to remote dispenser 3000. A commercially available application, provided by the distributor, may be used in accordance with well-known principles to exchange data between central server 2000 and mail order/prescription bottler system 7000.

Formulary System

As described above, the preferred method for importing and maintaining formulary files on the central server 2000 is to import and maintain formulary data files 8000 provided in any convenient format. Such files can be transferred and managed using any well-known data storage medium, or they may be transferred and managed using a direct network connection between central server 2000 and the publisher of the formulary data files.

Patient Visit and Prescription Process—Overview

Figure 3:
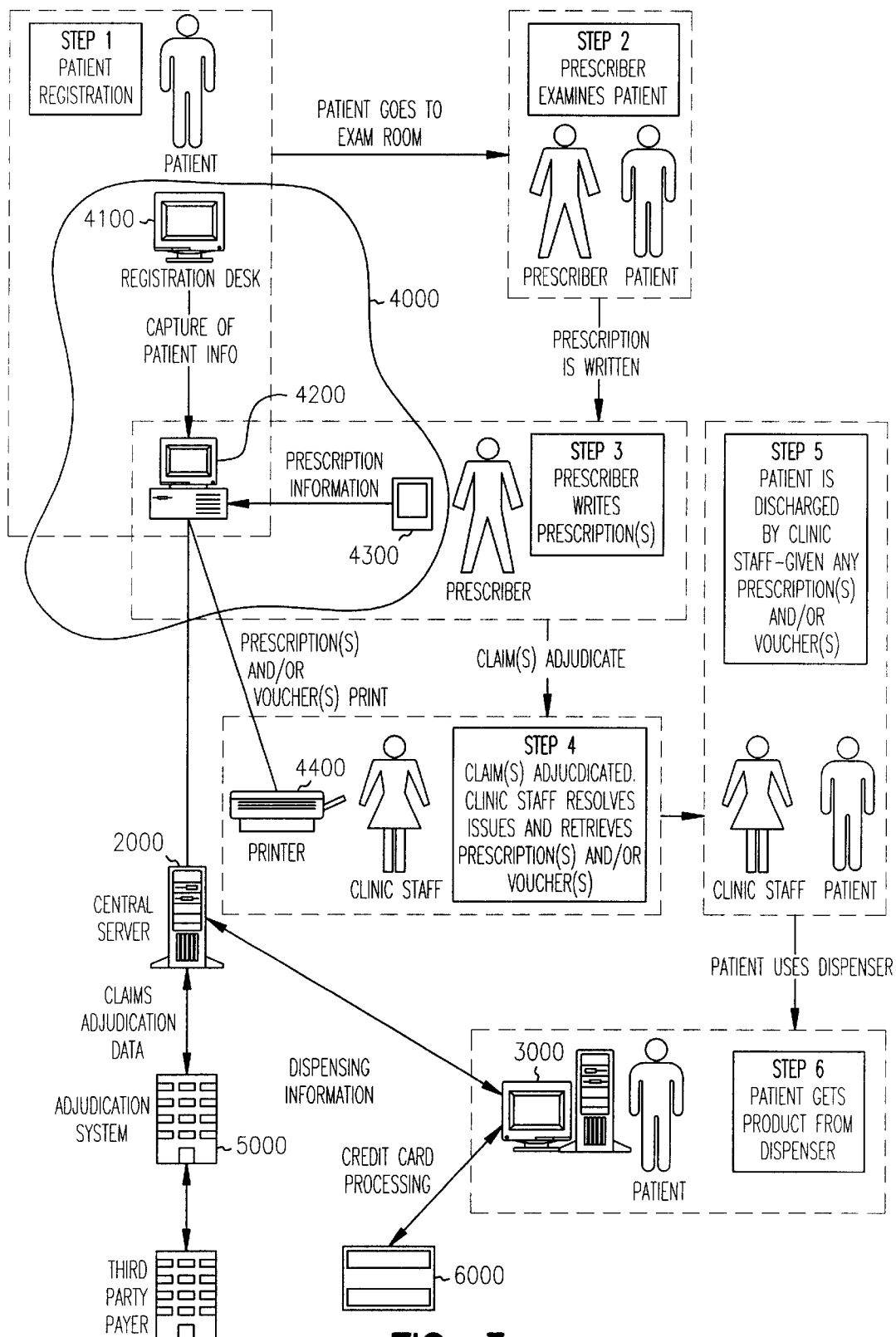
FIG. 3 is a schematic diagram of one embodiment of the process by which a patient is seen by a prescriber, receives a prescription, and has the prescription filled by the remote dispenser of the present invention.

FIG. 3 illustrates the basic process by which a patient is seen by a prescriber, receives a prescription, and has that prescription filled by remote dispenser 3000. In the patient registration process, the patient presents himself or herself at a registration desk where patient registration client 4100 is located. Patient information is captured by patient registration client 4100 and transferred to clinic workstation 4200. In the examination process, a prescriber (typically a physician) examines the patient and, depending on the outcome of the examination, may desire to prescribe a product for the patient. In the prescription writing process, the prescriber uses the handheld terminal 4300 to write a prescription by entering the prescription data into the handheld computer 4300 and transferring the data to the clinic workstation 4200. In the adjudication process, data representing the prescription and associated insurance information of the patient is sent by the clinic workstation 4200 to the central server 2000 for processing and subsequent transmission to the adjudication system 5000 under the control of a "switch" company that routes the prescription information to the proper third party payer. The adjudication system 5000 transmits data regarding the outcome of the adjudication to the central server 2000, which processes it accordingly and notifies the clinic system 4000 of the outcome. If necessary, the clinic staff resolves any outstanding issues and retrieves the adjudicated prescription and/or voucher from printer 4400 of clinic system 4000. In the discharge process, the clinic staff transfers the prescription or voucher to the patient as part of terminating the examination process. In the prescription retrieval step, the patient uses cash, a voucher or their card at the remote dispenser 3000 to have their prescription filled. This process involves the remote dispenser 3000 communicating with the central server 2000 for verification, inventory control, and other purposes.

Patient Registration Process

Figure 4:
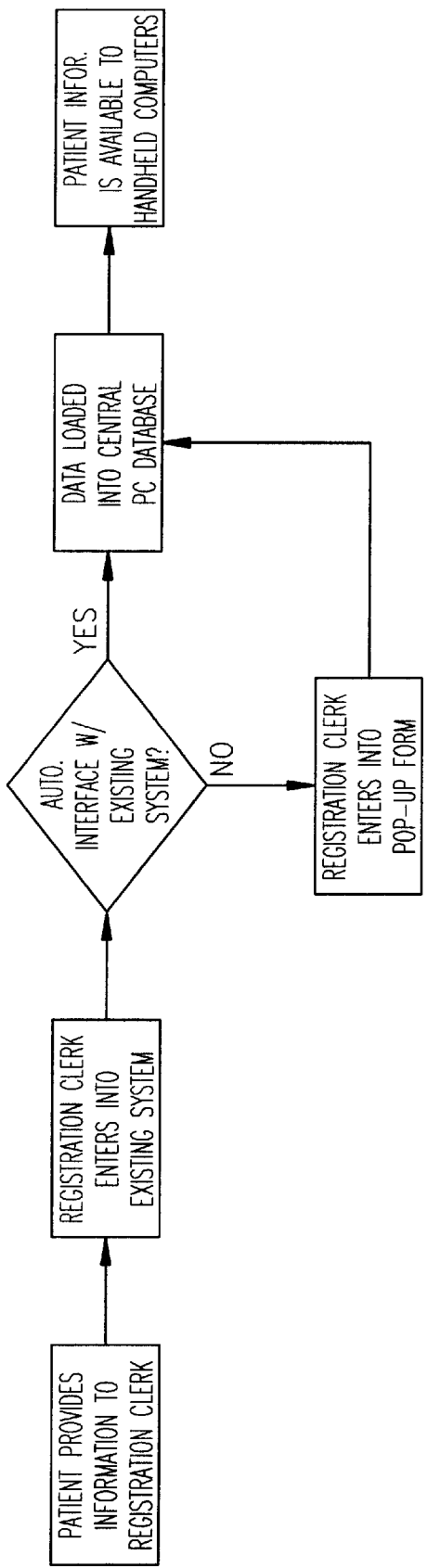
FIG. 4 is a schematic diagram of one embodiment of the patient registration process of the present invention.

FIG. 4 illustrates the patient registration process in more detail. The patient provides basic information to the registration clerk or the information is retrieved from a patient database. Such data would typically include mandatory information (name, gender, date of birth, mailing address, and telephone number) and optional information (social security number; weight; known allergies; prescriber name; prescription benefit insurance company name, policy number, group number, member number, and relationship code). Either the patient registration client 4100 contains an automatic interface to an existing registration system, or an application that captures the necessary information for the first time, or the information is manually entered into the system or the information is faxed or scanned to a remote location for manual entry, or some combination of the above. In either case, the captured data is immediately transferred to clinic workstation 4200, central server 2000, and subsequently to the specific handheld computer 4300 in use by the specific prescriber assigned to the patient.

Prescription Writing Process

Figure 5A:
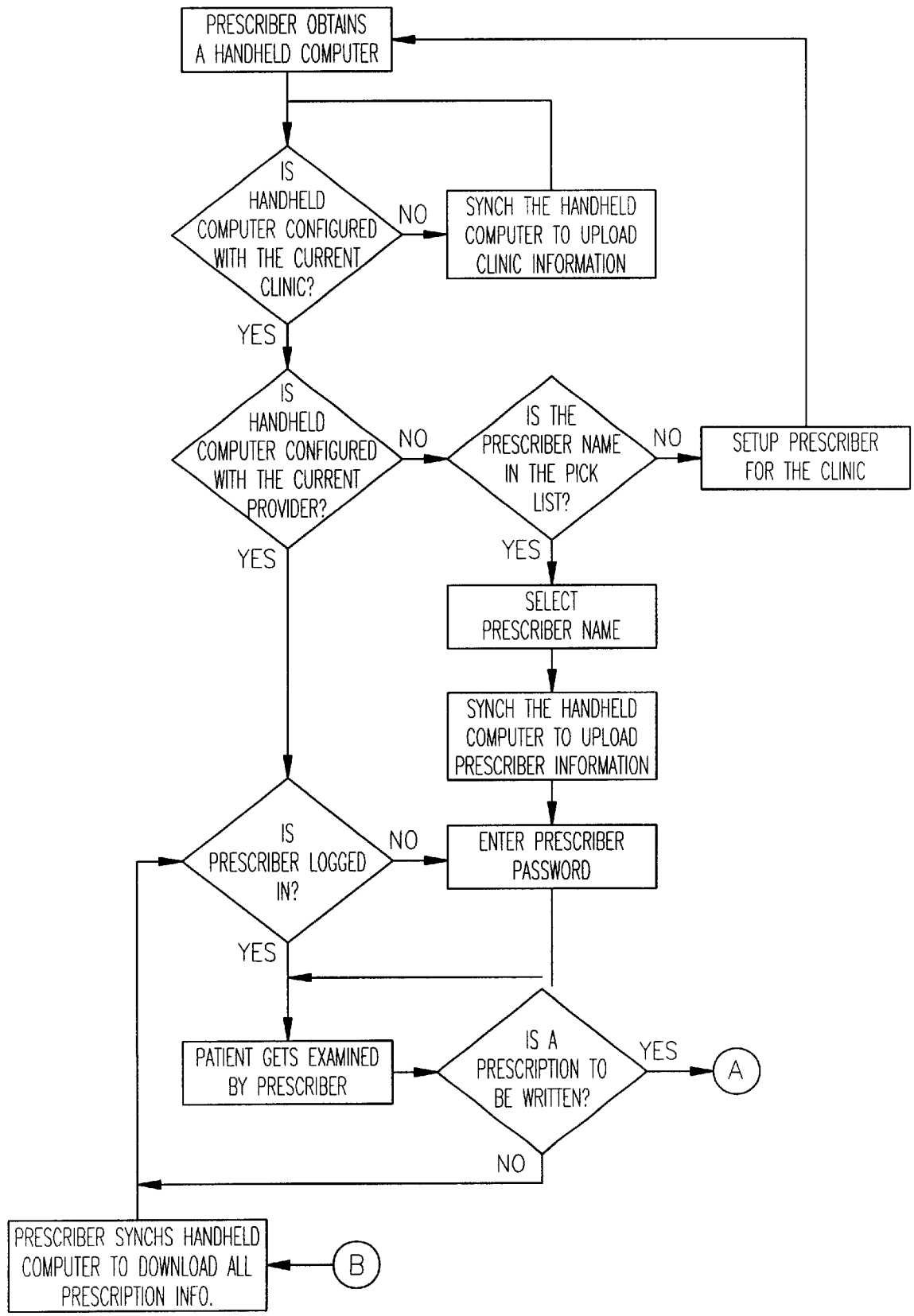
FIG. 5 is a schematic diagram of one embodiment of the prescription writing process of the present invention.
Figure 5B:
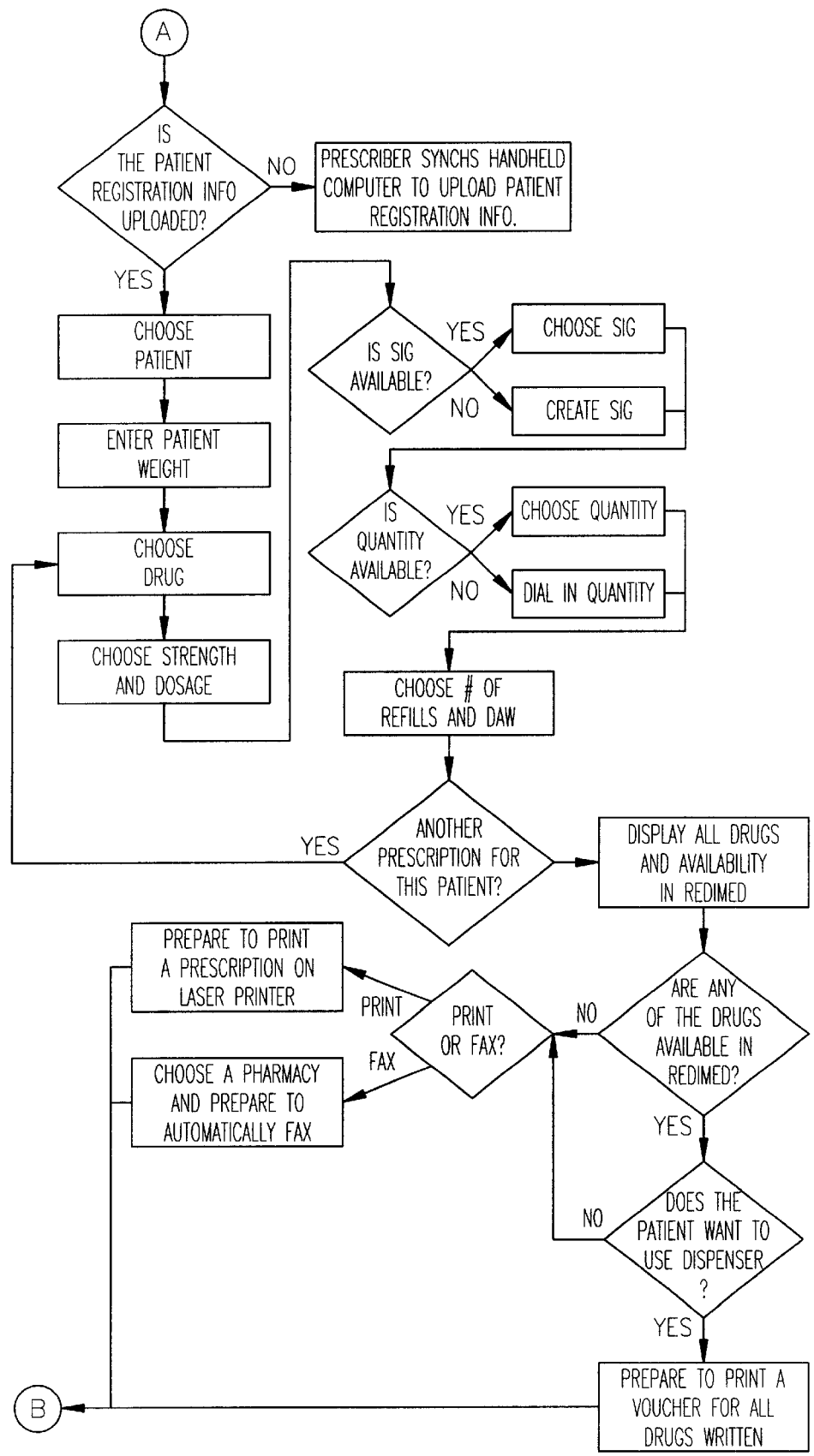

FIG. 5 illustrates the prescription writing process in more detail. The prelude to the specific process of writing a specific prescription is for a prescriber to obtain a handheld computer 4300 suitably configured for the patient that is about to be examined by the prescriber. The prescriber confirms whether the handheld computer 4300 is properly configured with information pertinent to the clinic in which it is located, a process that could occur once each day when the prescriber first arrives at the clinic. If not, a well-known synchronization (or, more commonly, a "sync") of the handheld computer 4300 to the clinic workstation 4200 or directly to the central database server will configure the handheld computer 4300. A similar process is required for confirmation whether the handheld computer 4300 is configured with information pertinent to the current prescriber, a process that could occur if prescriber uses a handheld computer 4300 that is resident at that particular clinic and shared between multiple prescribers. Once the clinic and prescriber are both properly configured in the handheld computer 4300, the prescriber performs a password-based login process. The sync may occur via infrared frequency or may occur automatically via a number of wireless technologies.

The prescriber examines the patient and decides whether to prescribe a product. If so, the prescription writing module is activated. First it must be confirmed whether the handheld computer 4300 is configured with information pertinent to the current patient. If not, a sync process is performed to retrieve the pertinent data from the clinic workstation 4200 or central database server. Once the handheld computer 4300 is ready to receive a prescription for the current patient, the patient's weight is entered, a drug is chosen, and strength and dosage of the drug are chosen. Since the patient's insurance plan is uploaded to the handheld computer along with other patient information, each drug viewed will indicate whether the drug is on the patient's insurer's formulary along with its approval status and whether the drug is in the remote dispenser. If the drug is not on the patient's insurer's formulary, the prescriber is prompted to a drug of the same therapeutic class that is covered on the patient's insurer's formulary. The prescriber may select a well-known SIG code for the product if one is available, otherwise one may be written by the prescriber. Similarly, if a standard quantity is available, it may be chosen, otherwise the prescriber may choose a quantity. The number of refills permitted without the patient requiring a new prescription is chosen, and the prescriber indicates whether the prescription is to be "dispensed as written," i.e., an equivalent generic drug can not be substituted in place of the specific brand of drug for which the prescriber has written. The prescription undergoes a drug utilization review (DUR). This includes drug-drug interaction, dosage range checking, patient allergy checking, pregnancy and lactation alerts and other safety checks. This entire process is repeated for the each product prescribed.

It is not necessary to limit the availability of products to only the remote dispenser 3000 located at that particular clinic. The handheld computer 4300 is able to indicate current inventory status of all remote dispensers 3000 because the sync process has given it extremely timely inventory information from the central server 2000 by way of the clinic workstation 4200. The prescriber may then determine from the patient whether the patient desires any of the products available from any of the remote dispenser(s) 3000 convenient to the patient's current location, or home, or other eventual destination. If so, the prescriber notes this on the handheld computer 4300 so that a voucher may be generated. If not, the patient is given the option of receiving a printed traditional prescription that may be taken to a pharmacy of the patient's choice, or if the patient identifies a particular pharmacy to receive it, the prescription may be transmitted directly to that pharmacy by facsimile, e-mail, or other communications channels. Regardless of the choice, a final synchronization of the handheld computer 4300 to the clinic workstation 4200 or central database server transfers the data to the clinic workstation 4200, the central system 2000, and the remote dispenser 3000 as appropriate. It is preferred but not required that this final synchronization also include updating the handheld computer 4300 with not only the current inventory levels of the remote dispenser 3000 in the local clinic, but also the information pertinent to the next patient scheduled to be seen by the prescriber.

Patient Discharge Process

Figure 6:
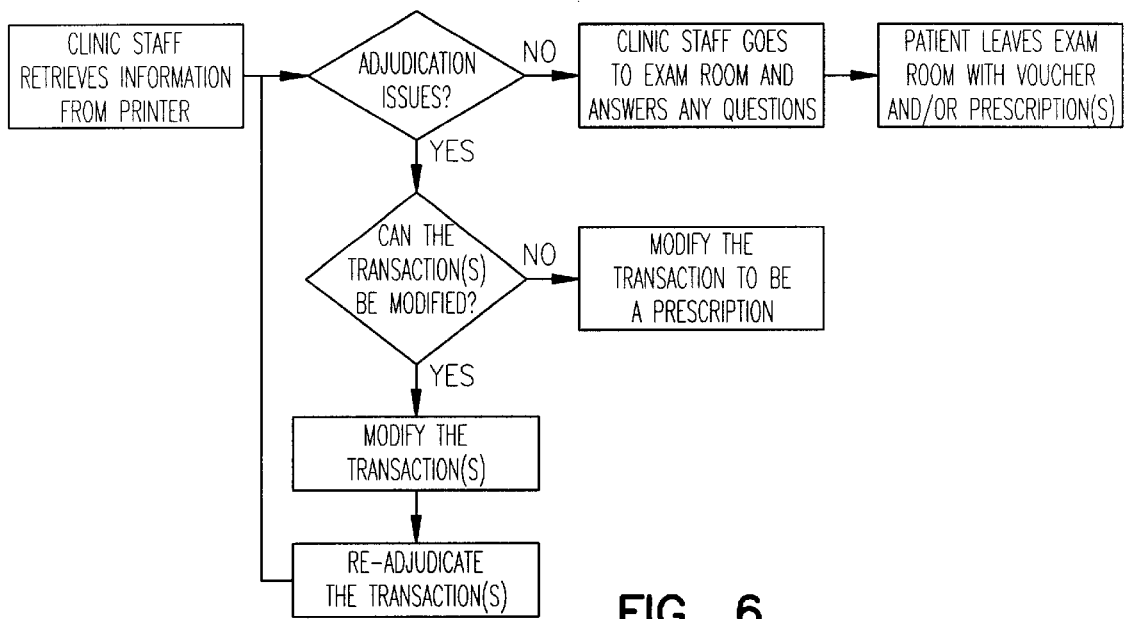
FIG. 6 is a schematic diagram of one embodiment of the patient discharge process of the present invention.

FIG. 6 illustrates the patient discharge process in more detail. The clinic staff receives information on the adjudicated prescription from the printer 4100 and determines if there are any outstanding issues remaining from the adjudication process. If so, it may be possible to modify the transaction to permit re-adjudication, or if not the transaction is modified into a traditional prescription that cannot be filled by any of the remote dispensers or communicated to a pharmacy of the patient's choice via facsimile, e-mail or other forms of communication. Either the traditional prescription or the adjudicated prescription (in the form of a voucher printed at printer 4100 and redeemable at the remote dispenser 3000) is taken to the examination room and presented to the patient after any outstanding questions from the patient are answered. Or, if the clinic prefers, the patient may receive either document upon leaving the clinic.

Prescription Modification Process

Figure 7:
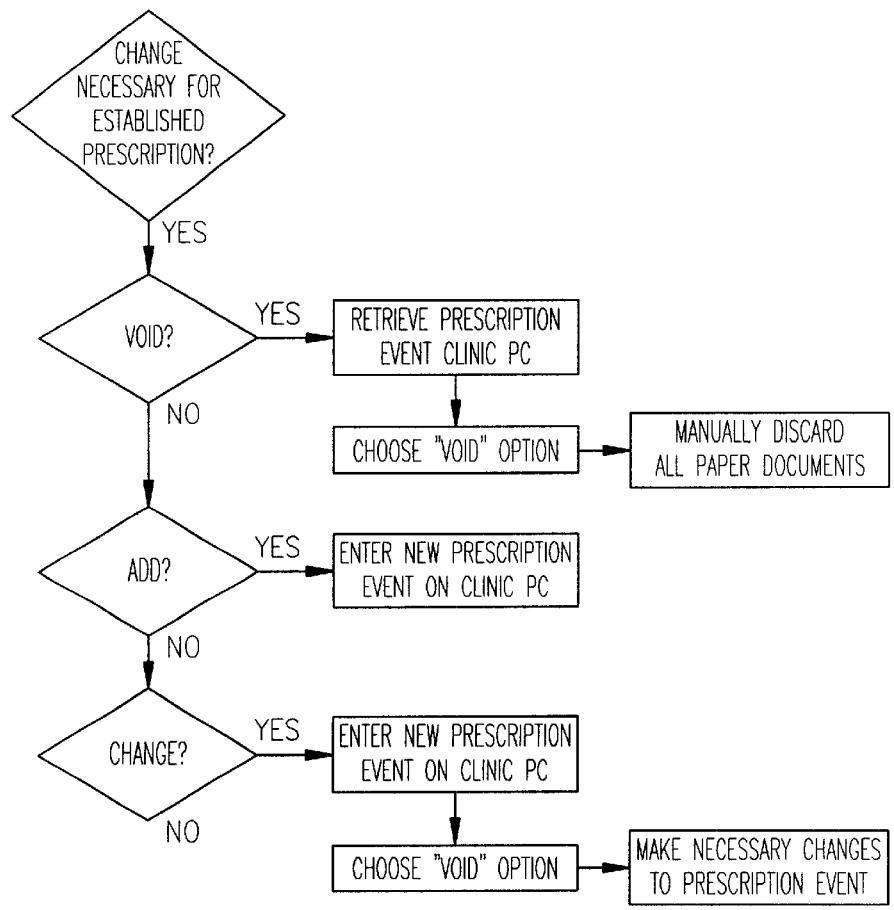
FIG. 7 is a schematic diagram of one embodiment of the process of modifying an established prescription of the present invention.

FIG. 7 illustrates the process of modifying an established prescription. To void an established prescription entirely, the entry is retrieved from the clinic system, a "void" option is recorded, and all paper documentation of the prescription is manually discarded. Additions or changes to an existing prescription are also entered on the clinic system.

Stock Ordering Process

Figure 8:
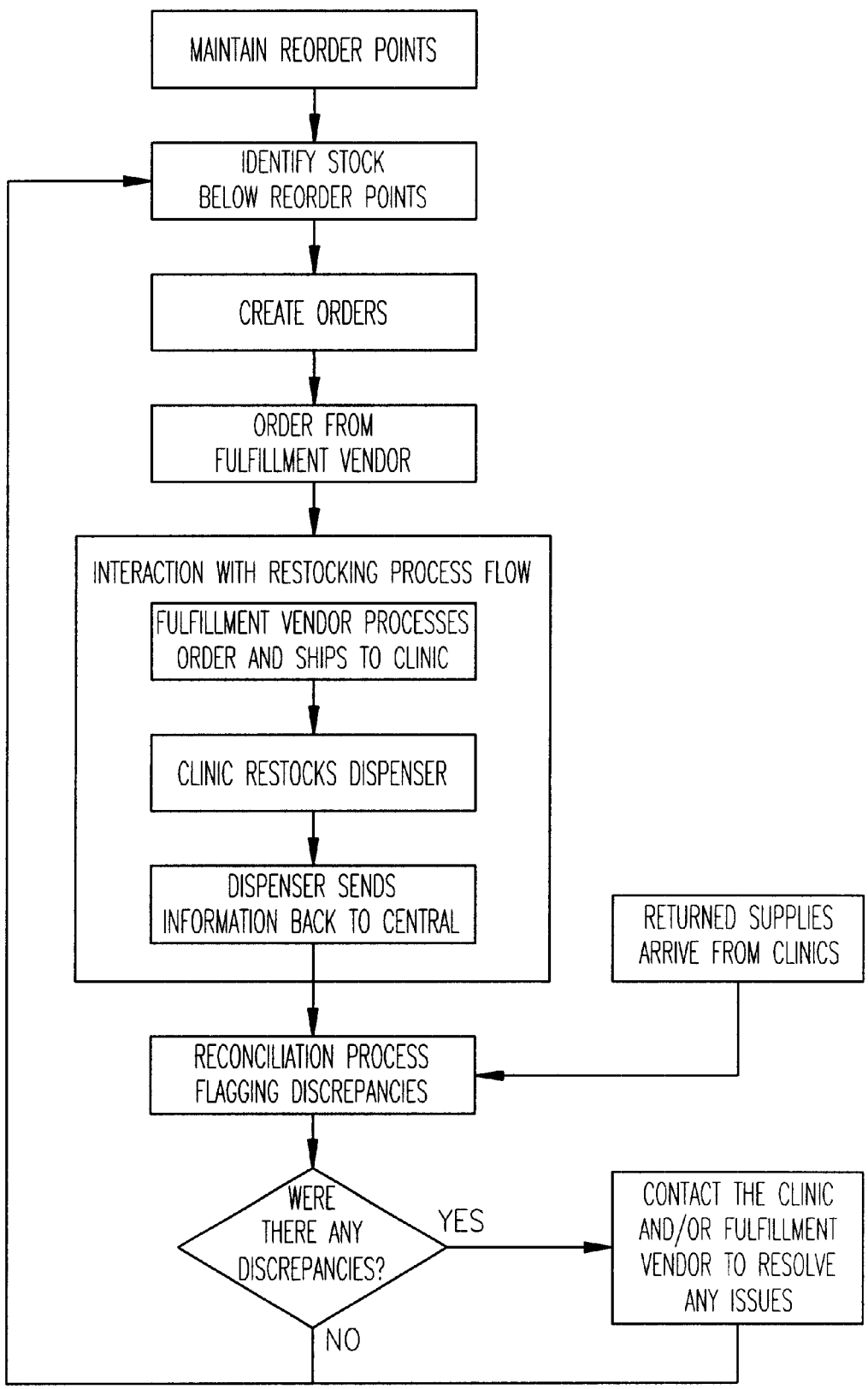
FIG. 8 is a schematic diagram of one embodiment of the process of ordering stock for each remote dispenser of the present invention.

FIG. 8 illustrates the process of ordering stock (either product such as prescription drugs or supplies such as labels and printer paper) for each remote dispenser 3000. Because all inventory data is maintained on the central server 2000, this process is executed there. In accordance with well-known inventory control principles, reorder points (quantities and/or dates to trigger reordering) are maintained for every stock item. When the actual inventory levels identify those stock items that are at or below their reorder points, orders for such items are generated and transmitted to appropriate fulfillment vendors. The central server provides orders for each clinic in addition to an aggregate order to the fulfillment vendor. The fulfillment vendor processes the order and ships the new stock to each individual clinic, even if the orders of each clinic have been aggregated together into a common order sent by the central server 2000. Personnel at each clinic or central personnel are responsible for restocking each remote dispenser 3000, and for returning any replaced or overstocked items, both as described in more detail below. Each remote dispenser 3000 automatically transmits updated inventory data to the central system 2000 where a reconciliation process identifies whether there are any discrepancies between anticipated and actual amounts and locations of each item. If there are discrepancies, they are identified and the clinic or vendor or both are notified so that all discrepancies may be resolved.

Restocking Process

Figure 9:
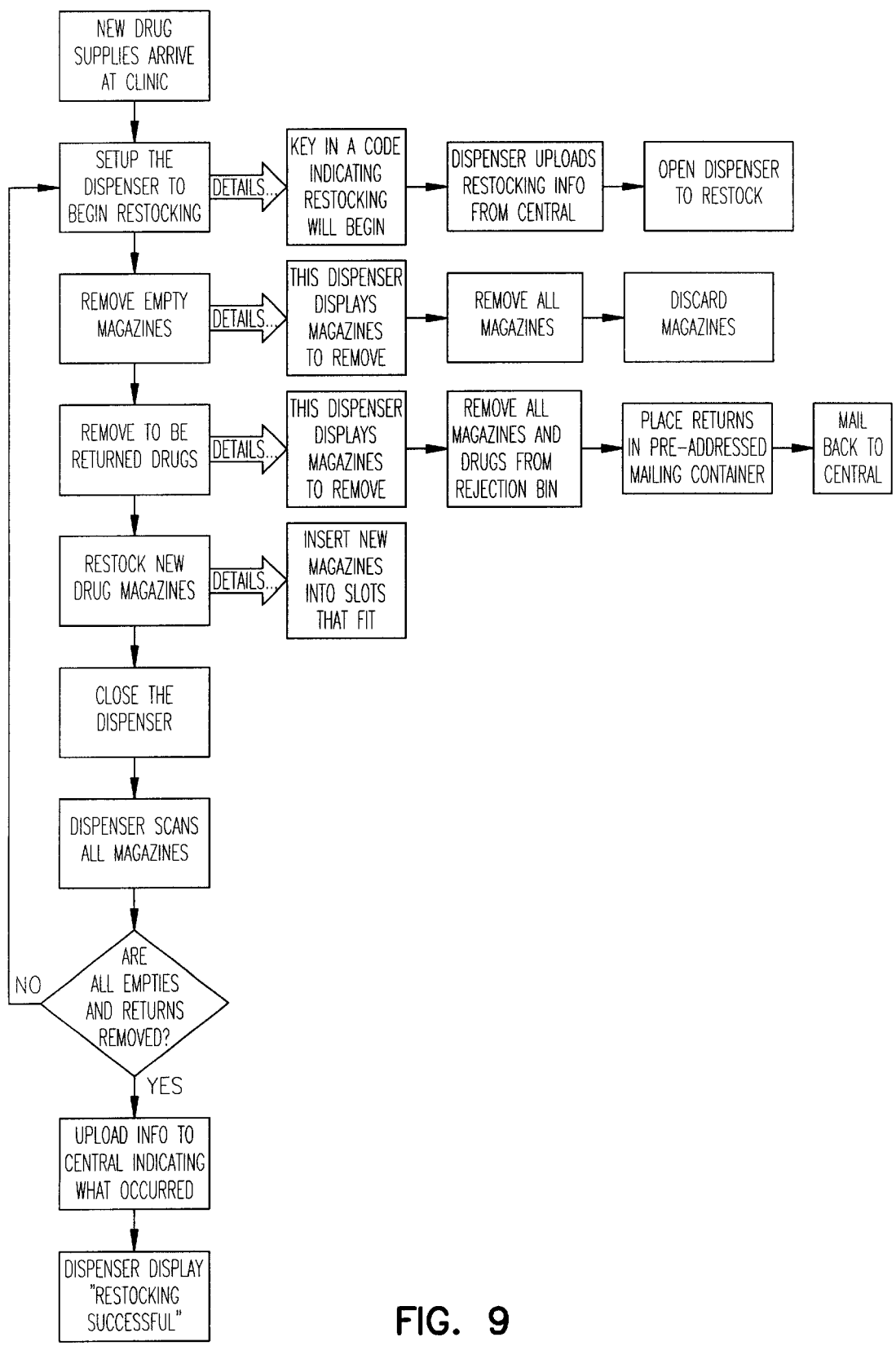
FIG. 9 is a detailed schematic diagram of the process of ordering stock for each remote dispenser of the present invention.

FIG. 9 illustrates in more detail the process of restocking each remote dispenser 3000. When new items arrive at the clinic, the remote dispenser 3000 is put into restocking mode, which is preferably accomplished by entering a specific code to activate the manager module to contact the central system for the most recent data relevant to the restocking process. Once such data is received, the portion of the remote dispenser 3000 dedicated to product inventory is unlocked and available for access. The first main task is to remove magazines that have been identified by the manager as empty of product, discarding the empty magazines themselves. Next, magazines that have been identified by the remote dispenser 3000 as containing products to be returned are removed. The individual products are removed from the magazines and returned, while the emptied magazines are discarded. Then, magazines containing new supplies are installed as required. Once the portion of the remote dispenser 3000 containing the products is closed and locked, the manager module 3200 scans all magazines to confirm whether all empty magazines and all magazines containing products to be returned have been removed. If not, the restocking process is not complete and must be re-performed. If so, data representing the current inventory levels and the inventory transactions that have just occurred is transmitted to the central server. Once this is complete, the visual display 3450 confirms completion of a successful restocking process.

Prescription Fulfillment Process—Overview

Figure 10:
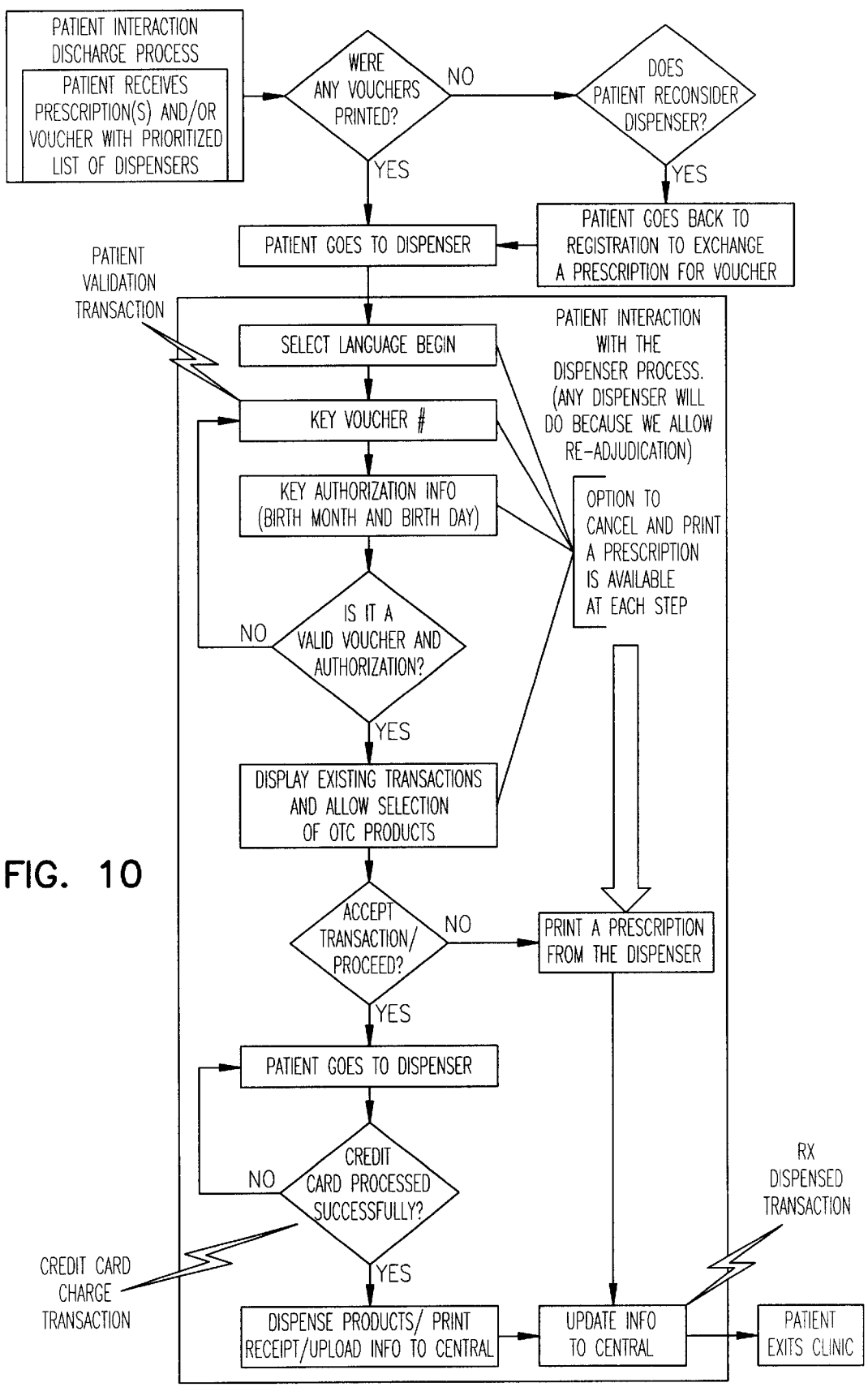
FIG. 10 is a schematic diagram of one embodiment of the process by which a patient has a prescription filled by the remote dispenser of the present invention.

FIG. 10 illustrates the basic process by which a patient has a prescription filled by remote dispenser 3000. In the patient discharge process, the patient either received a voucher for a product located in the remote dispenser 3000, or they may exchange a traditional prescription for such a voucher. Once in possession of a voucher, the patient begins by selecting a language in which the remainder of the exchange with the remote dispenser 3000 will take place. Then the patient enters the unique voucher number printed on the voucher along with patient authorization data (such as birth day and birth month, but this is only an example). The manager module 3200 determines whether the voucher number is valid and if so whether it properly correlates with the authorization data that the patient has entered. If not, the entry process is repeated in case erroneous data has been entered through simple human error. At this or at any other point in the process prior to acceptance of the entire voucher-based transaction, there is an option to cancel the voucher-based transaction and print a traditional prescription on printer 3950 for the patient.

Once a valid voucher and set of authorization data have been entered, the visual display 3450 shows a summary of existing prescriptions to be filled and a selection of possible over-the-counter (OTC) products that may be dispensed from remote dispenser 3000 without a prescription. The patient selects which if any products they wish to receive from remote dispenser 3000. The patient purchases their selections by passing a credit card through credit card reader 3850. Manager module 3200 receives data from the credit card through credit card reader driver 3800 and transmits it to central server 2000 so that the transaction may be conducted with credit card server 6000 in a well-known manner. As is common in the art, this may involve a repeated entry of credit card data by the patient for a variety of well-known reasons. Once the credit card transaction is authorized, manager module 3200 directs dispenser module 3100 to dispense the proper products. Manager module 3200 then prints a receipt on printer 3950 for the patient to take with them along with their products. Manager module 3200 then sends updated inventory and transaction data to central system 2000.

Remote Dispenser

Figure 11:
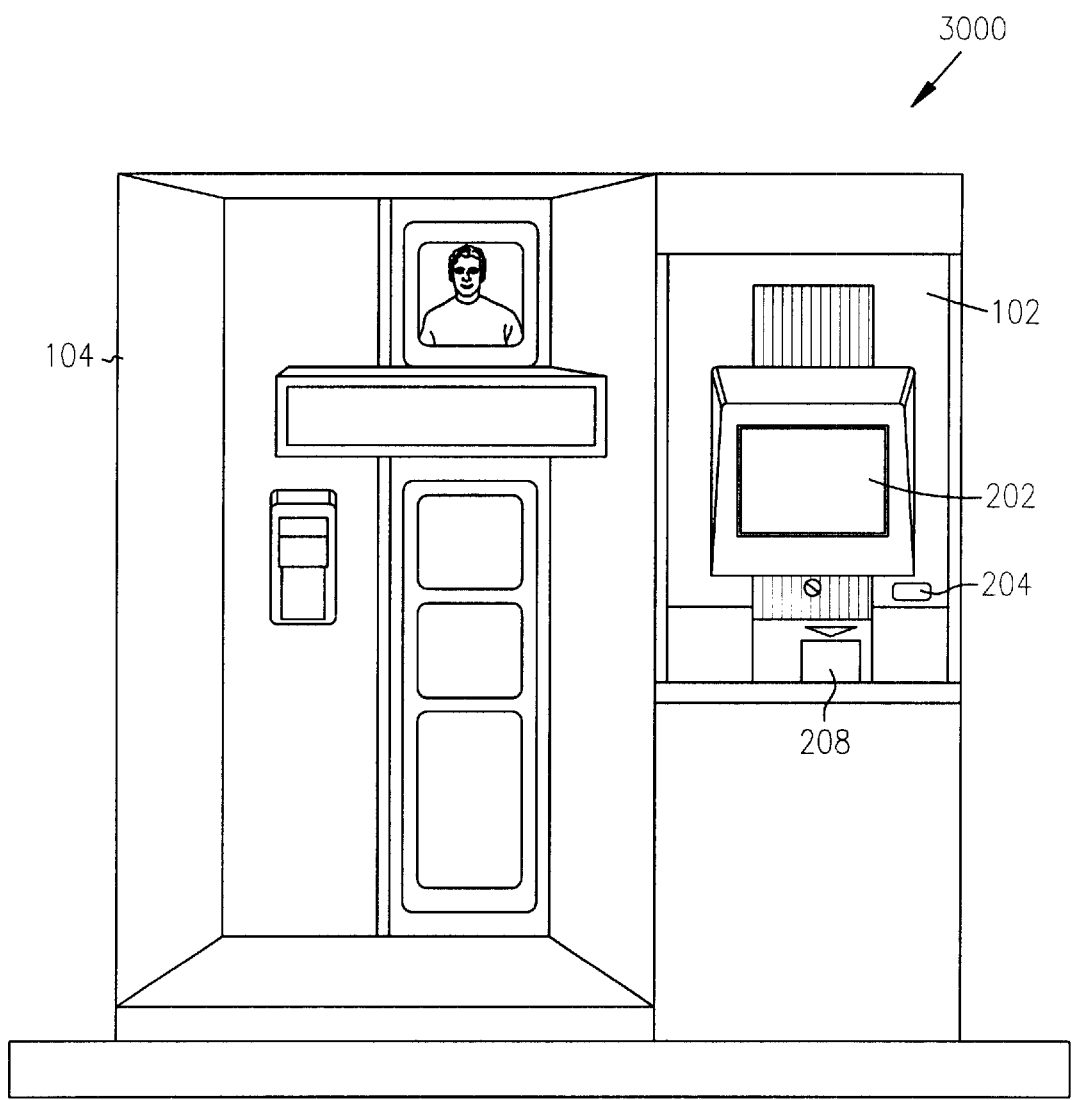
FIG. 11 is a front view of one embodiment of a remote dispenser of the present invention.
Figure 12:
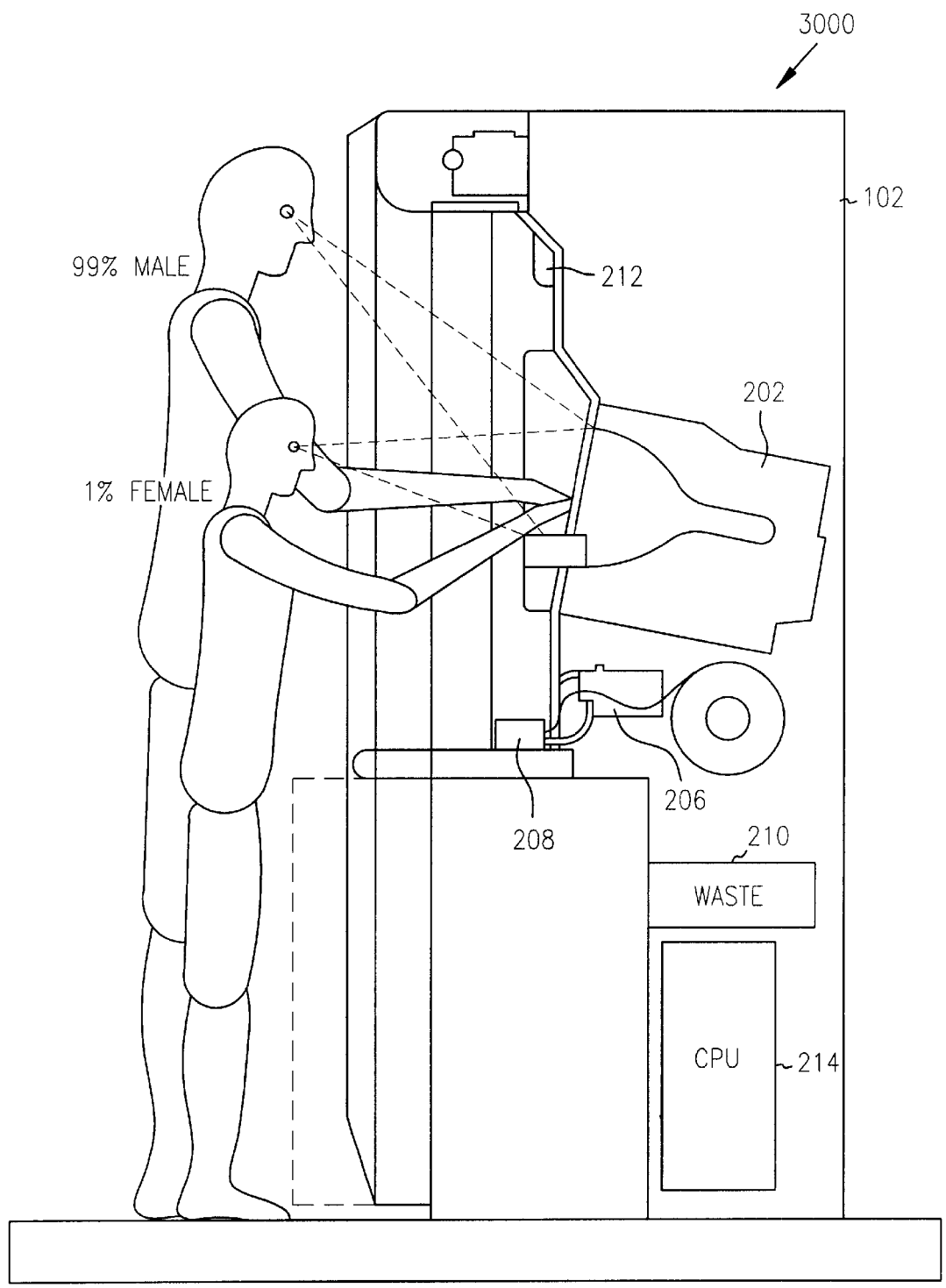
FIG. 12 is a side cross sectional view of the remote dispenser of the present invention.

As shown in FIG. 11 and FIG. 12, the remote dispenser 3000 consists of a control module 102 and a cabinet module 104. Optionally, the control module and cabinet module may be housed in a single cabinet. The basic configuration includes one control module and one cabinet module. Alternatively, an additional cabinet module may be added for increased drug storage capacity.

The control module 102 houses subsystems that provide the interface between the remote dispenser 3000 and the medical patient. These components include a 17 inch Monitor with touch screen 202, a credit card reader 204, a prescriptions/instructions/receipts printer 206, a prescription/instructions/receipt output slot 208, an internal waste slot/waste basket 210, speakers 212, and a controller PC 214.

An example of hardware and software that are suitable for the controller PC 214, which is located in the control module, is a Dell OptiPlex GX110 Mini-Tower having the following specifications: GX110 Pentium III processor, 500 MHz, 512 half speed cache & Integrated NIC; Memory: 128 MB Non-ECC SDRAM (1D IMM); Keyboard: Quietkey (Space saver); Video Solution: Integrated Intel 3D graphics with Direct AGP and 4 MB Display Cache; Hard Drive: 10 GB EIDE (7200 RPM); Floppy Drive: 1.44 MB 3.5; 4 (Min) PCI/ISA Slots; 2 (Min) serial ports; Dimension: Tower with Max size: 18 H×17 L×8 W; Extra Parallel Port Card; Sound Card: Sound Blaster Audio PCI (64 Voice), use with CD, DVD or CD-RW; CDROM; Network Card: Integrated 3Com EtherliNk 10/100 with ACPI and Remote Wake-up Only; and Operating System: Windows NT 4.0 Workstation SP5 with CD using NTFS. Other generally equivalently performing hardware and software could be substituted in a known manner without limiting the scope of the invention. In accordance with known principles, the design of the system should be such that the system functions are not dependent upon the particular hardware or software selected for implementation, thus permitting the system to migrate to other hardware or software platforms without any change in the scope of the invention.

The credit card reader/acceptor 204 is preferably from IDTech Company. Other generally equivalently performing hardware and software could be substituted in a known manner without limiting the scope of the invention.

The prescription/instruction/receipt printer is preferably a Datamax Ovation 2!, Direct Thermal Printer, and is located in the control module. The printer uses the same paper to print prescriptions, instructions and receipts on 4"×5" sheets. The patient information sheets are automatically trimmed to the proper length. The printer also prints product return packing slips and miscellaneous inventory transaction reports.

The remote dispenser 3000 is equipped with a temperature sensing subsystem (not shown) having both over temperature and under temperature set points. The central server is alerted if the temperature exceeds the set points.

Figure 13:
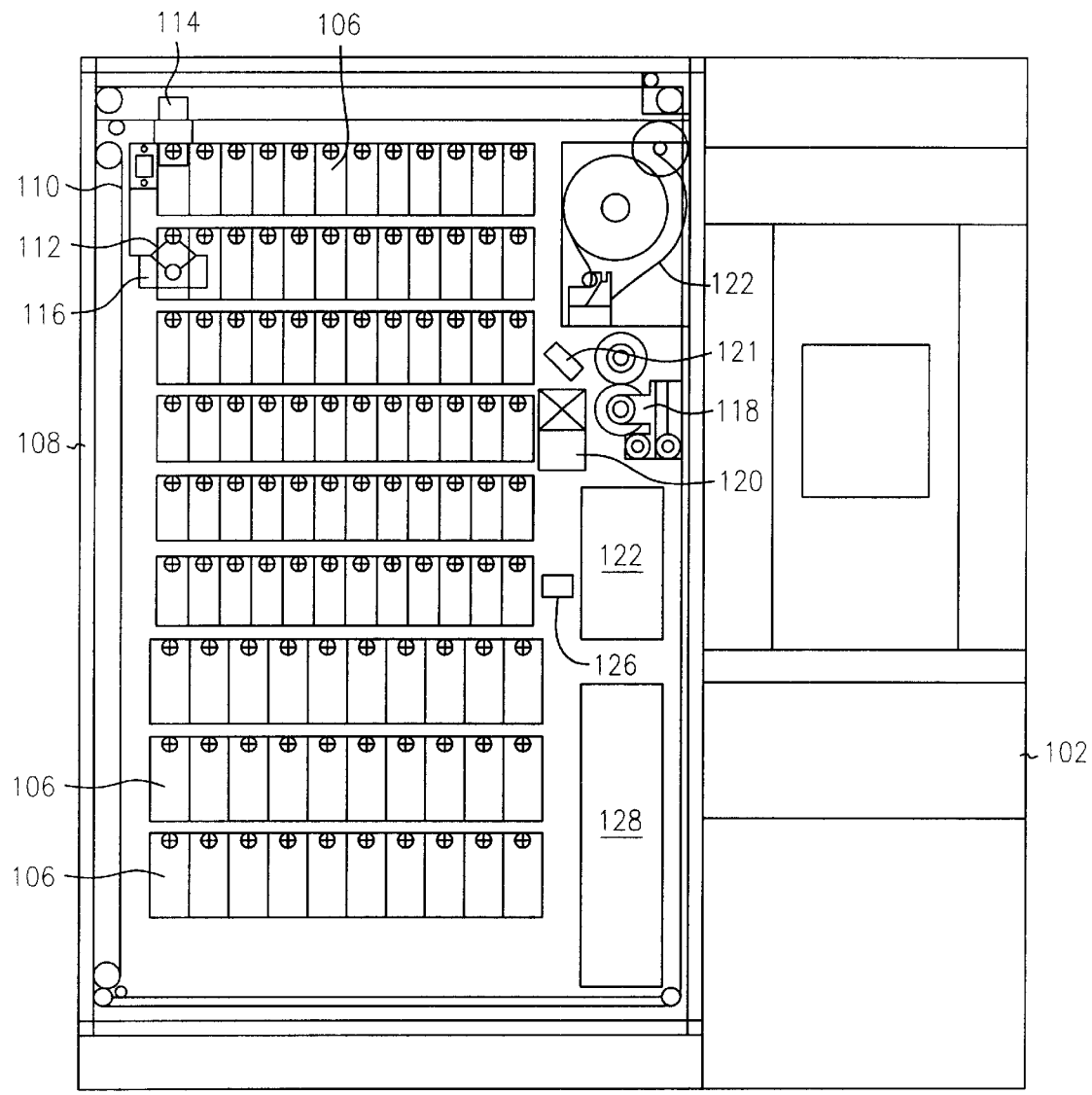
FIG. 13 is a front cross sectional view of the remote dispenser of the present invention.

As shown in FIG. 13, prescription drug products are stored in the cabinet module 104 in pre-filled magazines 106 that are mounted on cantilevered lead screws. The products are delivered to remote dispenser 3000 in the pre-filled magazines 106 and dispensed from the magazines. A cabinet 108 encloses the cabinet module 102. The cabinet module also stores product prior to dispensing and has a hinged door. The cabinet module also encloses the gantry transport system 110, product rotator 118, label printing system 122, and an uninterruptible power supply (UPS) (not shown). The UPS allows the remote dispenser to continue to function, in the event of power loss, long enough to complete any vending operation currently in progress and to achieve proper shutdown of the computer system.

The cabinet encloses a gantry system 110 that is used to position an end effector 112 and a magazine scanner 114, preferably a single directional scanner from PSC Company, model # LM520 single line laser scanner. Optionally, the remote dispenser may utilize a handheld scanner. The hand held scanner is stored inside the remote dispenser and may be used during restocking product.

The end effector 112 includes a product catcher 116 that transports the product from the magazines to a product rotator 118. The product rotator rotates the product for bar code reading by the bar code readers 120, 121 and application of the label by the label printer 122.

Bar code reader 120 is preferably an Omni directional scanner from PSC Company, model # VS800 Omni-directional laser scanner. The Omni-directional scanner 120 is located in the cabinet module and scans barcodes on the bottom of product. Bar code reader 121 is preferably a single directional scanner from PSC Company, model # LM520, single line laser scanner. Bar code reader 121 is used to scan the side of product while in the product spinner.

The label printer 122 is preferably a Datamax Ovation 2! having a thermal transfer ribbon attachment. Optionally, the printer may use a direct thermal technique. The label printer prints 2"×4" prescription container labels with bar codes and is compatible with the label applicator.

After the product is labeled, the product is dispensed through the product chute 124 by activating the chute door motor 126 or if the product is rejected it is sent to the reject bin 128. The product chute allows the packaged drug to be delivered to the patient at the remote dispenser, while preventing any individual from reaching into the chute to the point of being injured. Additionally, the control module is in a location proximate to the product chute where the product is dispensed to the patient.

The reject bin is a receptacle which stores products that do not pass the bar scan check. The packages are later removed and returned to the vendor.

Figure 14:
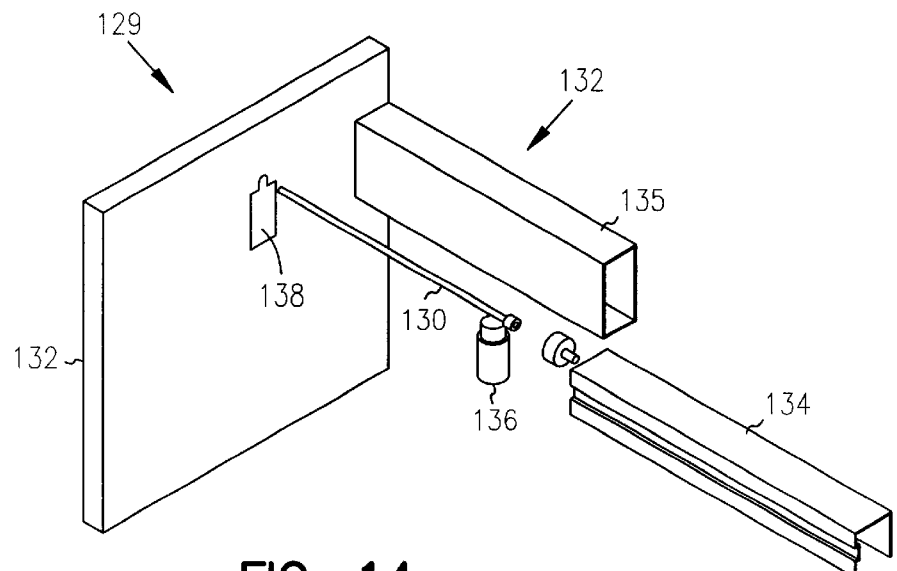
FIG. 14 is an exploded perspective view one embodiment of the magazine and lead screw system of the present invention.

FIG. 14 shows an exploded perspective view of the magazine and lead screw system 129. The cantilevered lead screws 130 are mounted to the inside back panel 132 of the cabinet module 104. The magazine 106 is mounted on the lead screw 130. The cartridge consists of a cardboard outer shell 132 and a vacuum molded inner portion 134. The product 136 is stored within the magazine 106. A pusher 138 for moving the product is threaded on the lead screw. The lead screw and pusher are mechanical elements designed to support the magazine within the cabinet module and to dispense product from the magazine. The lead screw is a threaded rod which, when rotated, causes the pusher to advance. The pusher is used to advance the product within the magazine assembly during the dispensing process. The magazine itself contains the product for a given magazine position (one specific product for a given position).

The magazine is a container that serves the dual purpose of a shipping carton and product-dispensing magazine. The magazine consists of three principle components: a corrugated (cardboard) paper outer shell 132, a vacuum-molded plastic inner liner portion 134, and a bar code label 135 placed on the outboard end of the magazine. The outer shell is a tube designed to support the inner portion during shipping and handling and during application inside the remote dispenser. The inner liner portion is designed to prevent the product from changing orientation during shipping and handling, as well as to align the magazine to the lead screw and to guide the products during the dispensing process. The bar code label is used to identify the contents of the specific magazine so that the appropriate preprogrammed dispensing procedure is affected. The exterior surface of the magazine may also contain a legible label stating the drug product content of that magazine. However, the barcode label on the outside of the magazine may have the drug product name printed in English in addition to the barcode or the product package is readable within the magazine.

Figure 15:
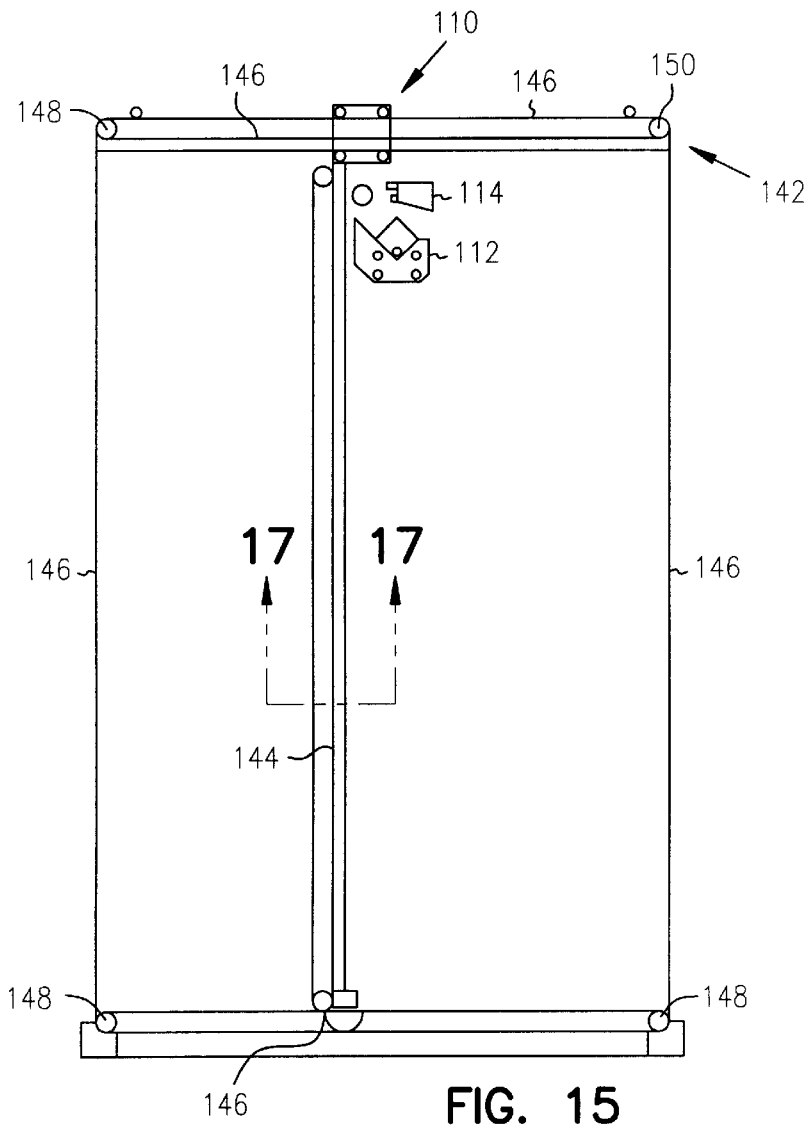
FIG. 15 is a front view of one embodiment of the gantry transport system of the present invention.

FIG. 15 is a side view of the gantry transport system 110. The gantry transport system 110 is a two-dimension robotic assembly used to position the end effector 112 at a given magazine position. Additionally, the gantry system transports the product from the magazine to the product rotator and label printer and also positions the magazine scanner 114.

The gantry transport system 110 includes an x-axis system 142 and an y-axis system 144. The x-axis system moves the y-axis system and the end effector 112 from side to side, while the y-axis system moves the end effector 112 up and down. The x-axis system includes an x-axis belt/cable 146, x-axis pulleys 148, and an x-axis motor system 150. The x-axis system consists of a belt 146 looped around pulleys 148 and a cable 146 looped around idler pulleys 148. The motor system 150 consists of a motor, gearbox power supply and controller. As the controller signals the stepper motor, the motor repositions the belts and cables and moves the y-axis system from side to side.

As shown in FIG. 16, the y-axis system consists of an y-axis belt/cable 152, y-axis pulleys 154, and an y-axis motor system 156.

FIG. 17 is a cross sectional view of the y-axis transport system. The y-axis system is supported on a frame structure 158. The frame structure consists of a Lexan rail 160 affixed to an aluminum tube 162. Guide wheels 164 aligned the y-axis system along rail 160.

Figure 18:
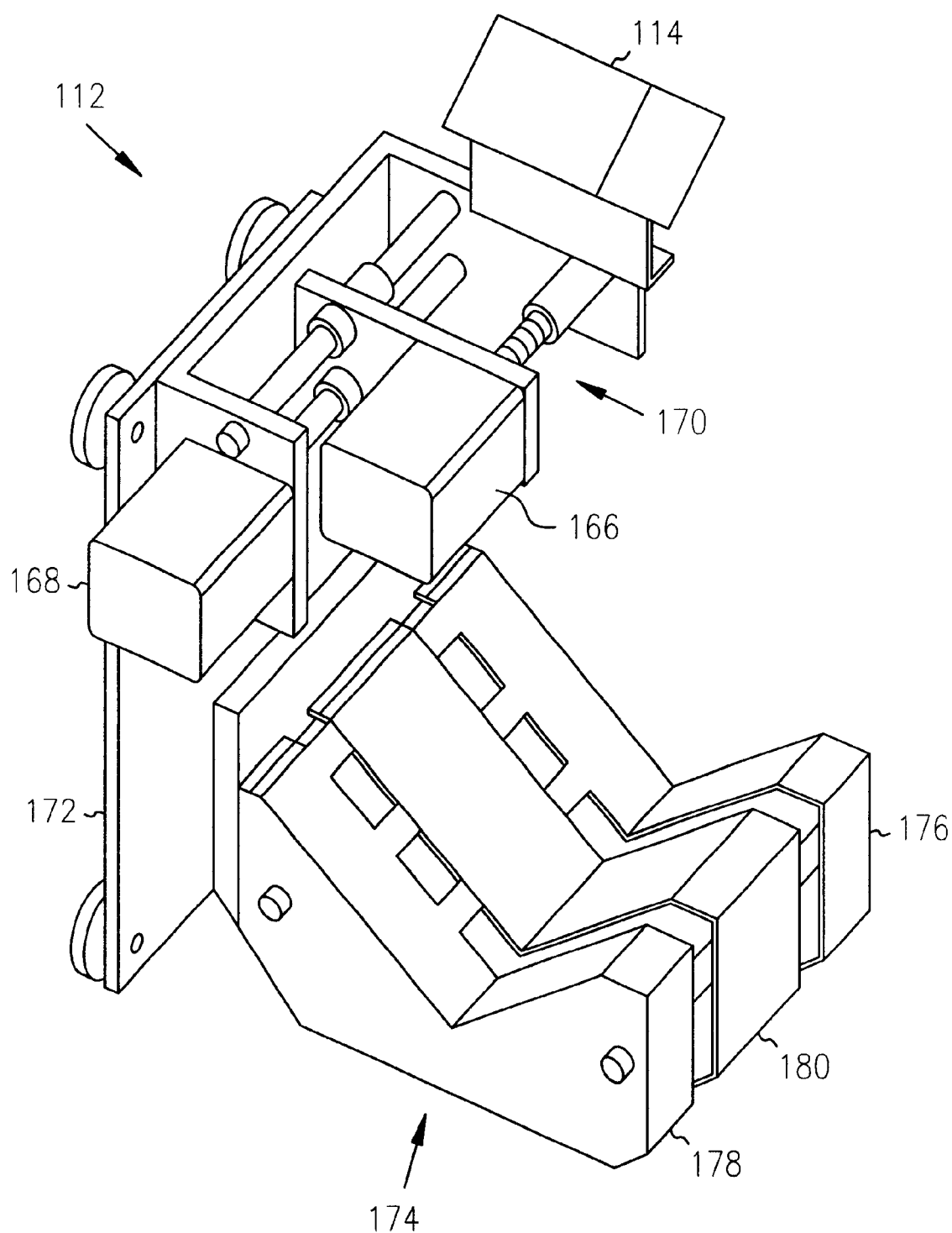
FIG. 18 is a perspective view of one embodiment of the end effector of the present invention.

FIG. 18 is a perspective view of end effector 112. The end effector is a mechanical device mounted on the gantry transport system and is used to retrieve and transport the product during the dispensing process. The end effector 112 includes a drive screw motor 166, a lead screw coupler motor 168, an optical sensor 170, a mounting plate 172, and a product catcher 174. The lead screw coupler motor 168 advances a drive adapter (not shown) to couple to the lead screw. Optical sensor 170, which upon detecting the "fall" of a product into the product catcher, signals the lead screw drive motor to stop advancing the product out of the magazine tube. The product catcher captures the product as it is advanced out of the magazine. The product catcher includes a stationary mitt 180, and outside moveable mitts 176, 178.

Figure 19:
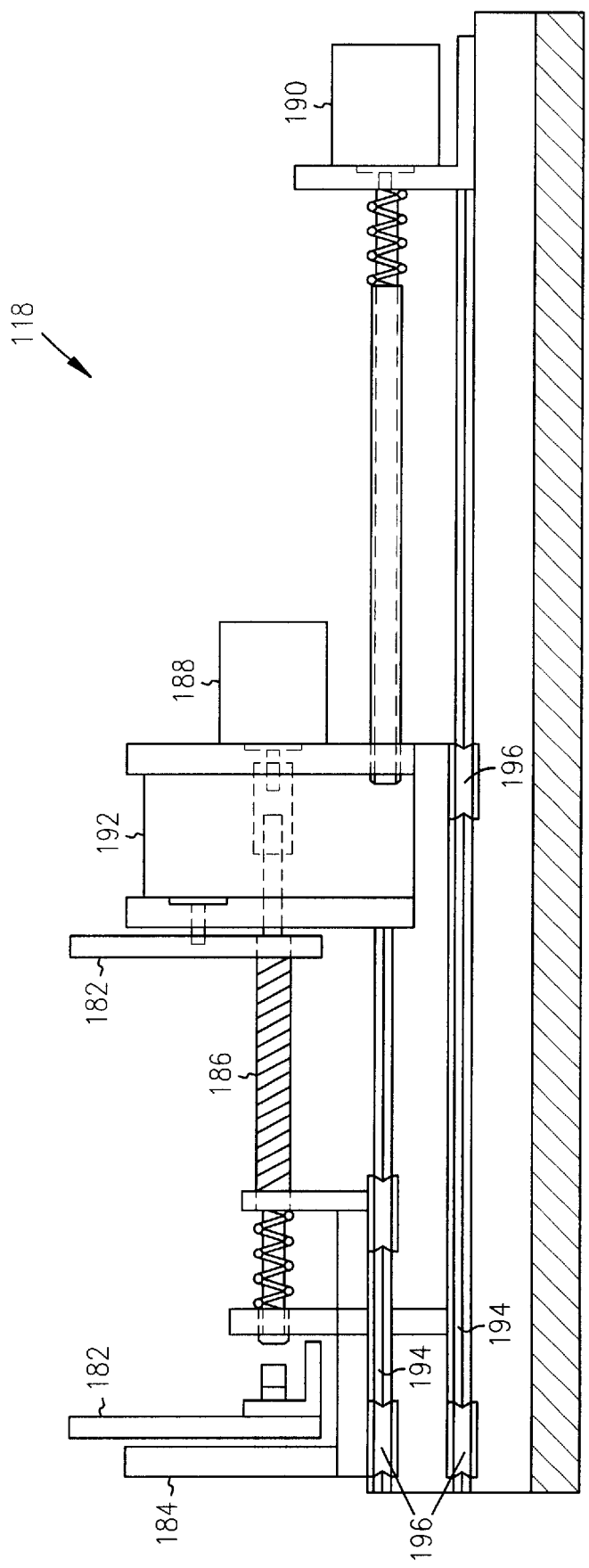
FIG. 19 is a side view of one embodiment of the product rotator of the present invention.

FIG. 19 shows a side view of product rotator 118. The product rotator serves the function of spinning the product in the barcode scanner beam, so that the product can be identified, and rotating the product as the product label is applied. The product rotator 118 consists of two rotating disks 182, one of which is mounted to a traveling arm 184 that is actuated by a screw 186 that is driven by motor 188. When the package is transferred to the product rotator, the traveling arm 184 is moved inward, the disks are brought together, and the package is captured between the disks. A second motor 190 then acts via a second screw to position the entire rotator mechanism under the label printer. A third motor 192 spins the disks and rotates the package to effect label application. The traveling arm 184 moves along rails 194 on guide wheels 196.

Figure 20:
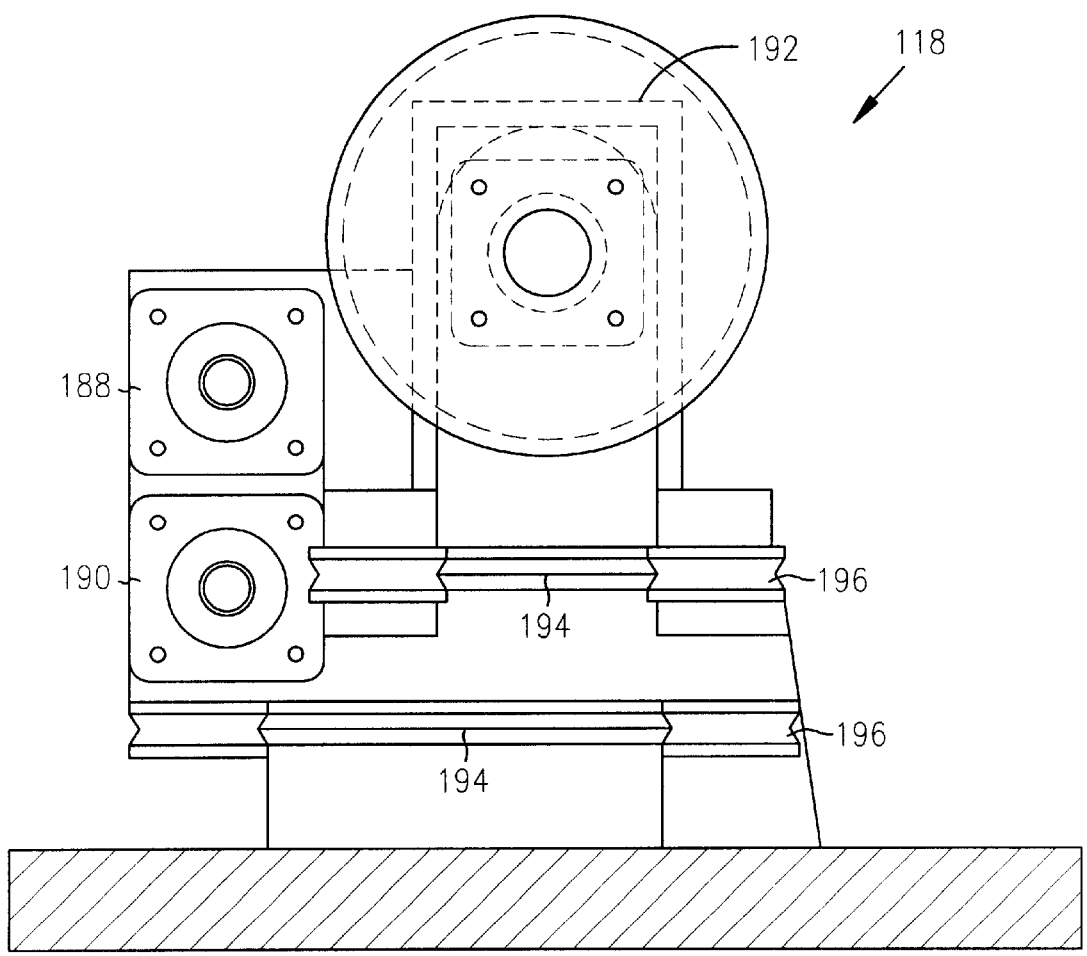
FIG. 20 is an end view of the product rotator of the present invention.

FIG. 20, shows an end view of the product rotator 118 showing the positioning of motors 188, 190, and 192 and the positioning of rails 194 and guide wheels 196.

Figure 21:
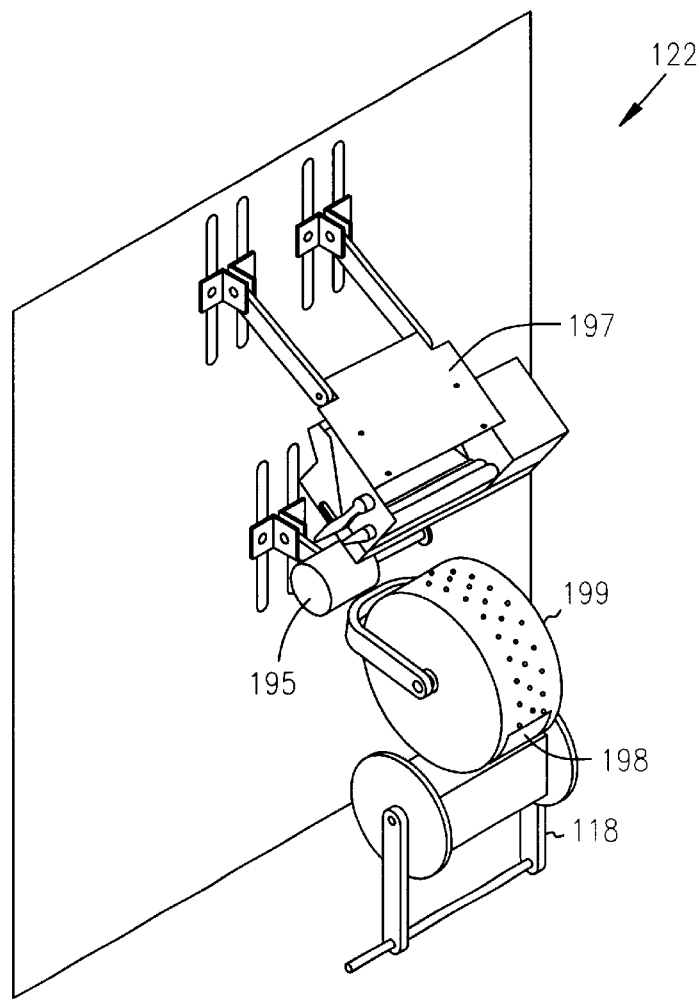
FIG. 21 is a perspective view of one embodiment of the label printer assembly of the present invention.

FIG. 21 shows a perspective view of label printer 122. The printer mechanism 197 generates an adhesive-backed package label 198 and advances the label toward a transfer wheel 199. The label 198 is held on the surface of the transfer wheel 199 by vacuum (adhesive side of label is outward) while the drive motor (not shown) advances the transfer wheel. A solenoid 195 retracts and allows the transfer wheel to swing to the product rotator 118 for label application. The label makes contact with the product package while the product rotator spins the package at which point the label adheres to and is transferred to the package.

Product Dispensing Process

The dispensing process will not initiate until the patient (or clinic staff) has entered all required information and the credit card and/or insurance payment has been verified for inputs required to allow drugs to be dispensed.

The sequence of events in dispensing a product is as follows:

1. The x- and y-axis gantry motors position the end effector in the correct magazine location. The lead screw positioner motor extends the coupler on the end effector toward the mating coupler on the lead screw, until the two couplers are intermeshed but not in contact, which prevents excessive loads from being transmitted to the cantilever lead screw assembly. A load sensor (e.g. a spring and a proximity sensor) is used to apply a known tip load on the cantilever lead screw assembly. The x- and y-axis gantry motors are then powered down to eliminate additional forces being exerted. The drive screw motor 166 then engages the coupler until the sensor detects the necessary load, after which the y-motor is powered up and lifts the end effector a pre-calculated number of steps to unload the lead screw bearing.
2. The drive screw motor 166 rotates the spring-loaded conical coupler/lead screw, advancing the pusher to dispense the product into the catcher of the end effector.
3. An optical sensor, positioned to detect the product as it falls into the catcher, signals the drive screw motor to stop advancing the product.
4. The product is transported via the end effector to the product rotator, where telescoping catcher is compressed by the product rotator. At the same time the product is then grasped and held between two rubber-faced disks, one idler and one driver disk.
5. The clamp pressure is controlled by preset position/calibration of a proximity sensor and compression spring displacement.
6. The product rotator rotates the package until scanned to verify that the correct drug is being dispensed. If the scan is successful, the remote dispenser completes steps 7 through 10 below. If the scan is not successful, the product is dropped into the reject bin and the process returns to step 1. If the scan reveals that the correct drug is not being dispensed, the magazine location is recorded, the clinic is alerted, and the process returns to step 1 at another magazine location for the same drug.
7. The label printer generates an adhesive-backed package label and advances the label toward the transfer wheel.
8. The label is held on the surface of the transfer wheel by vacuum (adhesive side of label is outward) while the drive motor advances the transfer wheel. A solenoid retracts and allows the transfer wheel to swing to the product rotator for label application.
9. The Product Rotator spins the package and the label on the roller is lowered onto the product package at which point the label adheres to and is transferred to the package.
10. The scanner checks the applied label to verify that the label was applied properly.
11. A flapper moves to divert the labeled package into the dispensing chute.
12. The rotator disks retract allowing the package to drop, and the product is directed to the package output portal of the remote dispenser.

Stocking/Restocking Process

Upon sending a new shipment of drugs to the remote dispenser, the product supplier also sends an electronic file, referred to as the product file that contains data on the contents of the shipment.

Preparing the remote dispenser for restocking consists of one or more of the following steps: a) Inserting a security code, b) Opening the cabinet door, c) Scanning the shipper bar code located on the outside of the shipping carton, d) Displaying the descriptions and locations of magazines to be removed and returned to the vendor including magazines that are empty or contain discontinued or outdated product, e) Removing all empty magazines, f) Removing magazines listed on the display and scanning the magazine barcode, g) Indicating if the correct magazine was removed, h) Displaying the status of the magazines by color, i) Scanning the barcode of each package from the return bin that is to be returned to the vendor as well as any packages that have fallen from the magazine to the bottom of the remote dispenser, j) Keying barcodes for packages that will not scan properly, k) displaying all scanned and keyed return products, l) Placing return products in a return shipping carton, m) printing a packing slip of return items and placing the packing slip in the return shipping carton for shipping to the vendor, and n) sending an electronic soft copy of the packing slip to the central server.

The process of refilling the remote dispenser consists of one or more of the following steps: a) Displaying the magazines in the new shipment, b) Scanning the barcode on each magazine from the new shipment, the barcode indicating the contents of the magazine, c) Displaying an indication that the magazine was received, d) returning unreadable or unlisted magazines to the vendor, e) indicating a refill location on the display, f) loading the new magazine in the refill location, g) guiding the new magazine onto the lead screw at the refill location, h) pushing the new magazine fully onto the lead screw assembly, i) closing the cabinet door, and j) automatically scanning the barcodes at the front of each magazine to confirm placement and location.

Figure 22:
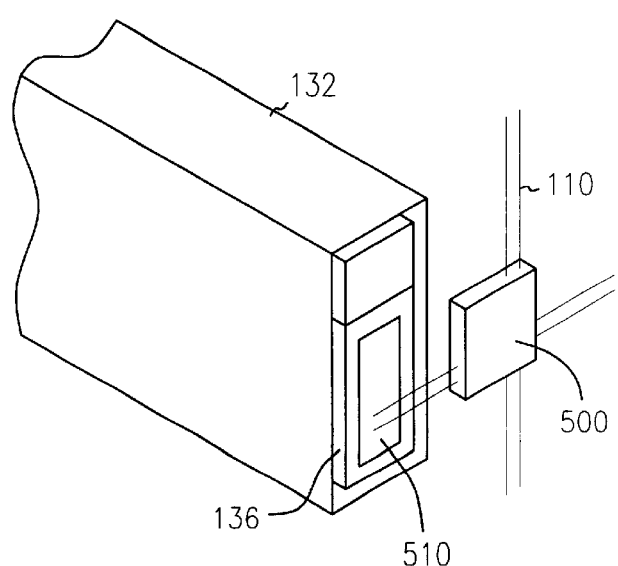
FIG. 22 is a perspective view of one embodiment of the moveable printer of the present invention.

FIG. 22 shows another embodiment of the present invention. A moveable printer 500 moves on the gantry transport system 110 as discussed above. The printer 500, such as an inkjet printer, directly prints on the package 136 or directly prints on a label 510 that is attached to the package 136. The packages 136 are stored in magazines 132 as discussed above. The package 136 is positioned at the end of the magazine to allow the printer to print on the label 510 on the product. Once the printing is complete the product is dispensed to the patient.

Palm Pilot Prescription Entry Program

The Palm Pilot Prescription Entry System allows new prescription entry using personal defaults, new prescription entries needing customization, new pediatric prescriptions, viewing, revising or deleting prescriptions already written, and revising a prescription when the insurance denies the prescription. The entry system is operated using the control buttons on the bottom edge of Palm Pilot 4300. As shown in FIGS. 23–30, Palm Pilot 4300 includes a tab button 4310, a cancel button 4320, a scroll button 4330, an enter button 4340, and a hotsync button 4350. Tab button 4310 is used to tab between screens. Cancel button 4320 is used to cancel or go back one field. Scroll button 4330 is a bidirectional button and is used to scroll up and down. Enter button 4340 is used to enter and to move to the next field. Hotsync button 4350 is used to provide a hotsync between the palm pilot 4300 and another device.

FIGS. 23–30 show exemplary screens of one embodiment of the Palm Pilot Prescription Entry Program.

Figure 23A:
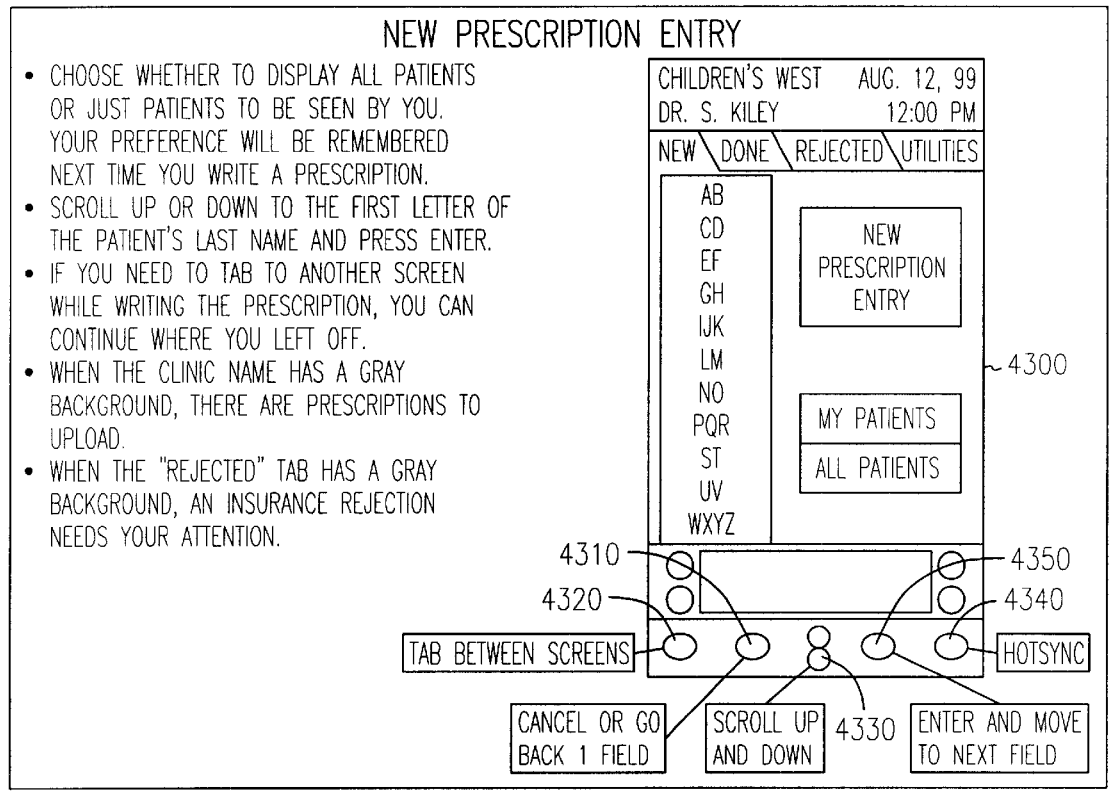

FIG. 23A shows an exemplary screen for new prescription entry. The user chooses whether to display all patients or just patients to be seen by the user. The preference is stored for the next time a prescription is written. The user scrolls down using scroll button 4340 to the first letter of the patient's last name and presses enter button 4340. The user optionally may tab to another screen while writing the prescription and return later to finish the prescription at the point where the user left off. When the clinic name 4360 has a gray background, there are prescriptions to upload. When the rejected tab 4370 has a gray background an insurance rejection has been received.

Figure 23B:
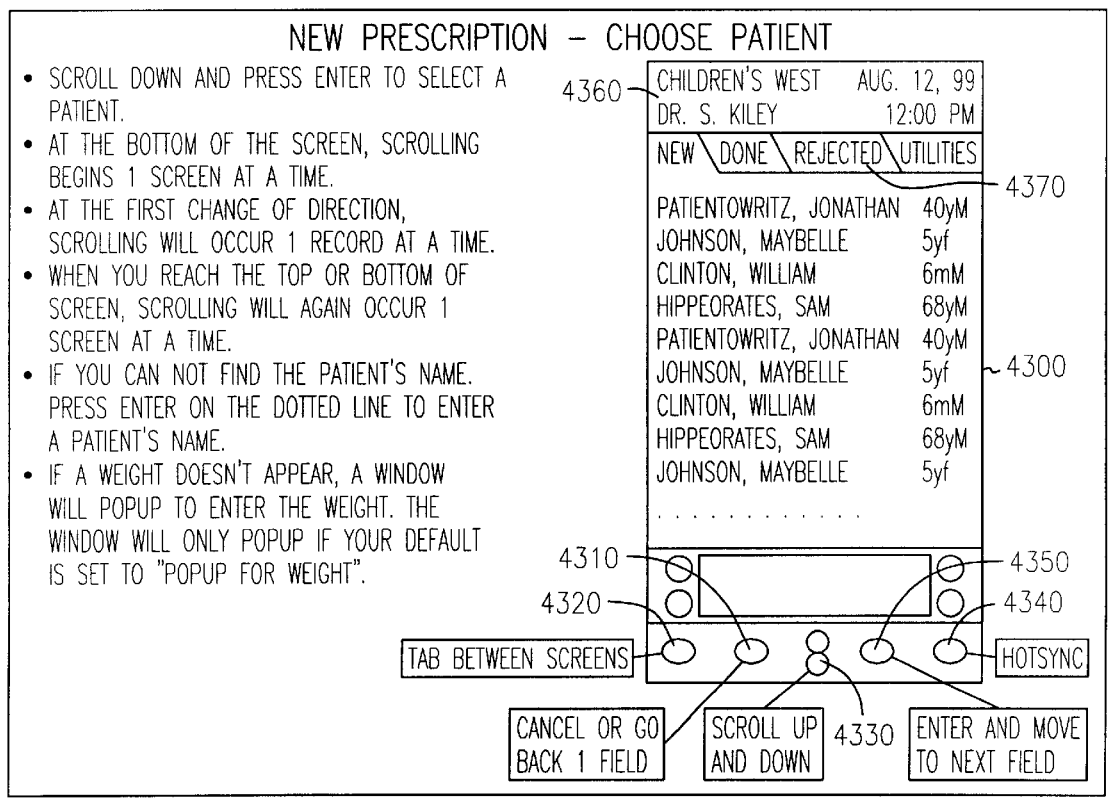
Figure 23C:
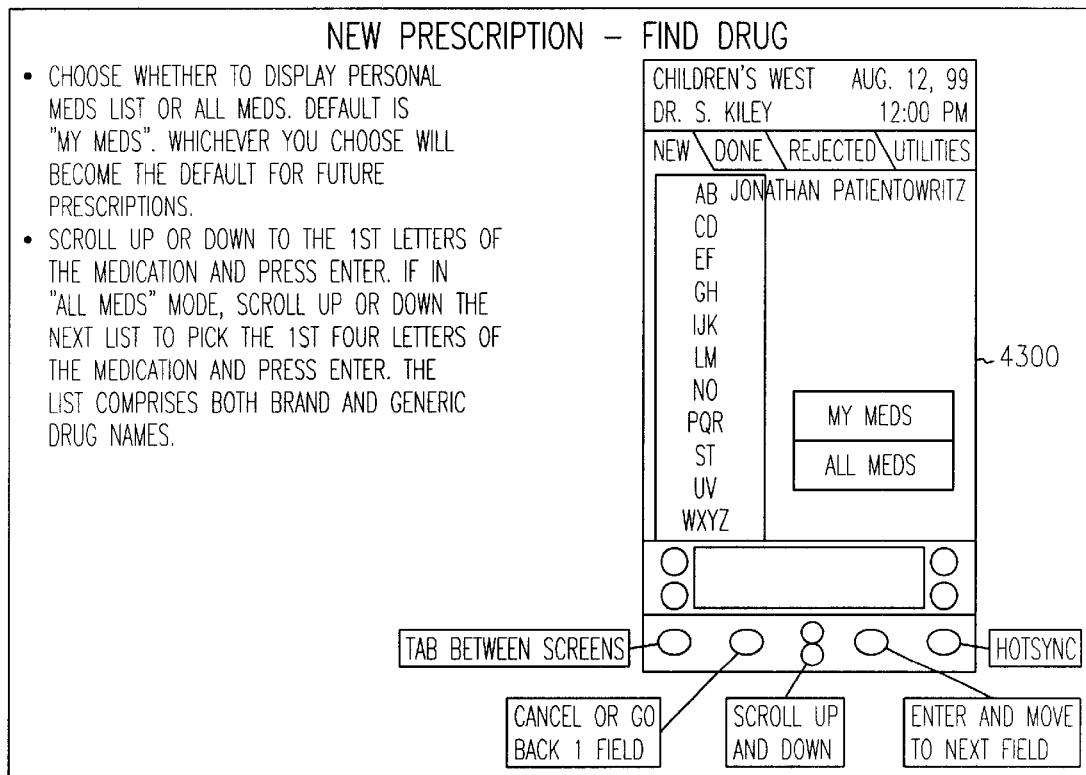
Figure 23D:
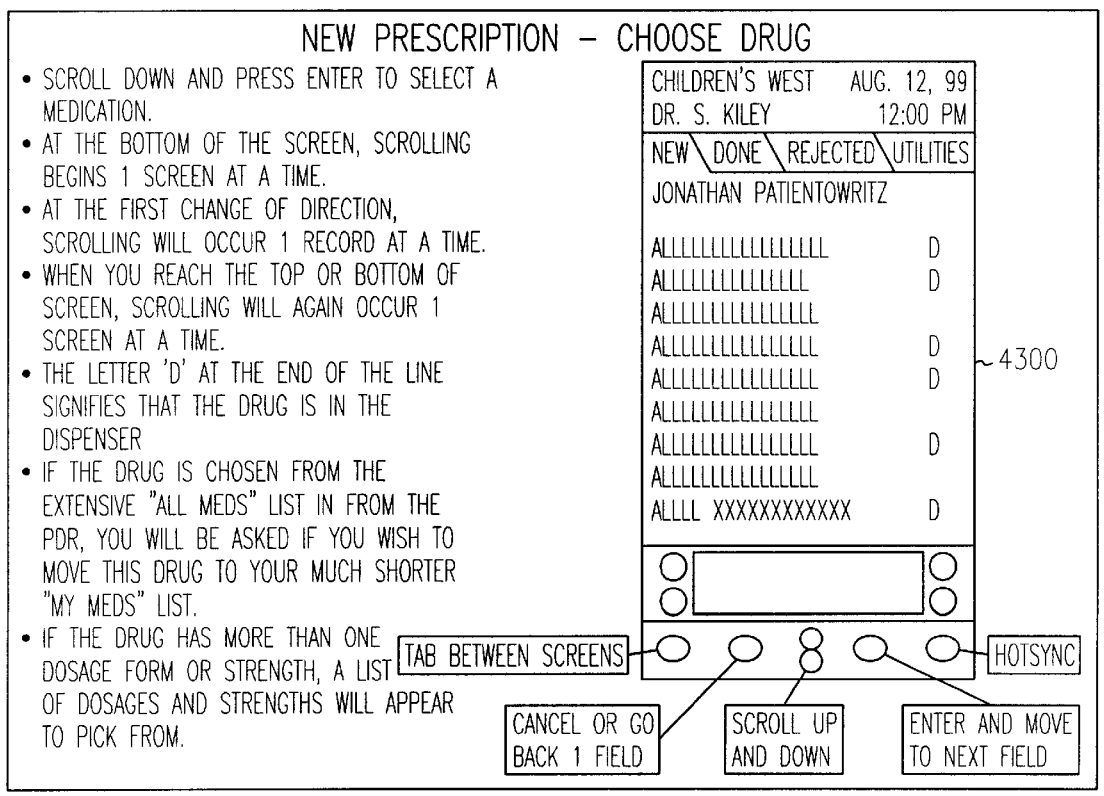
Figure 26B:
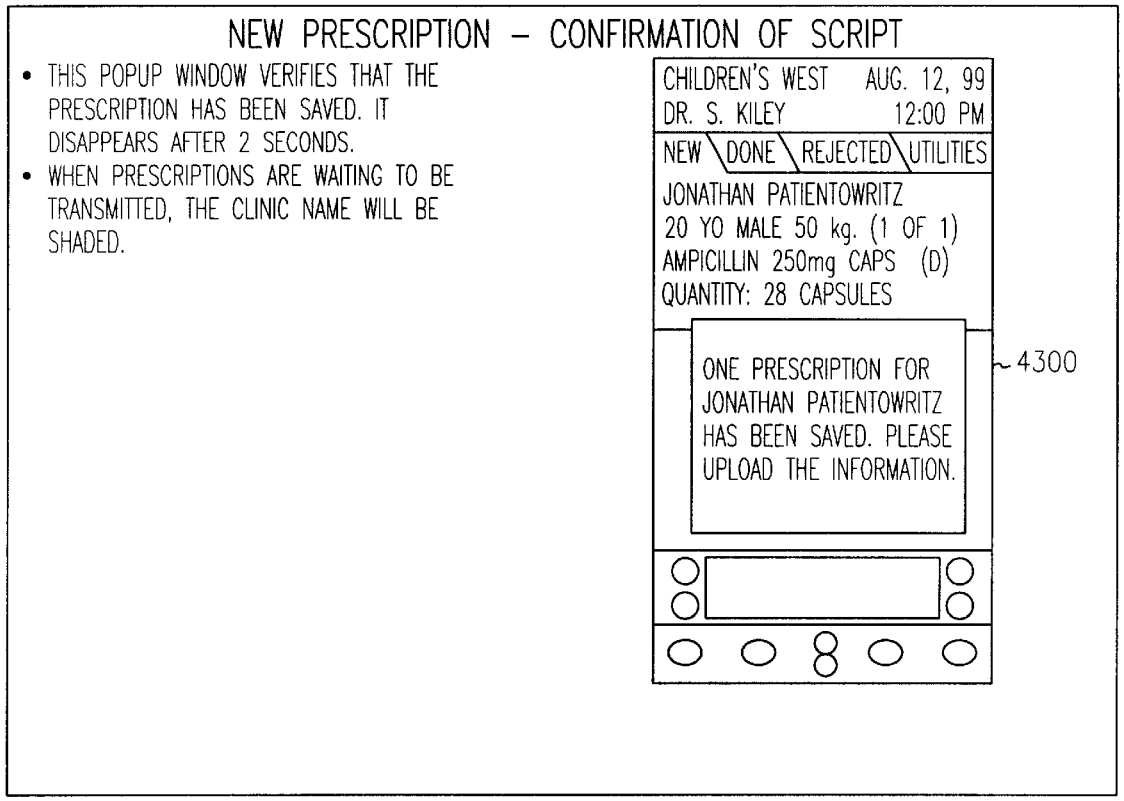
Figure 26C:
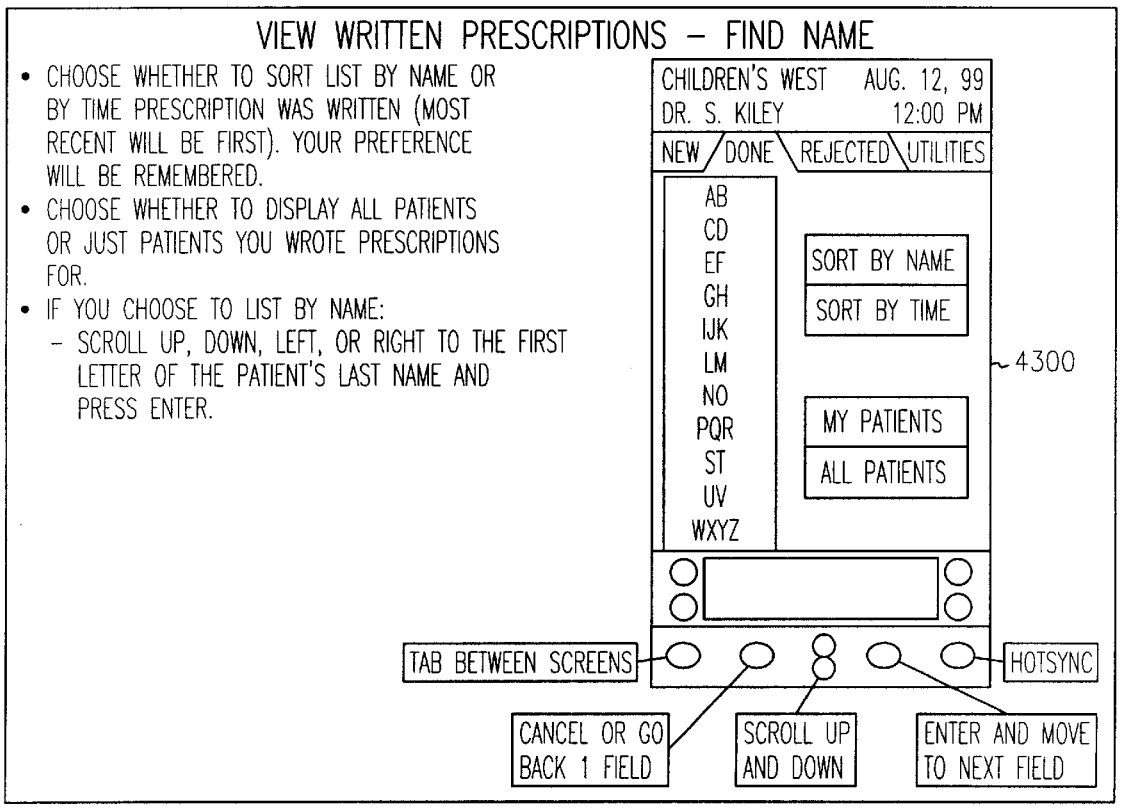
Figure 26D:
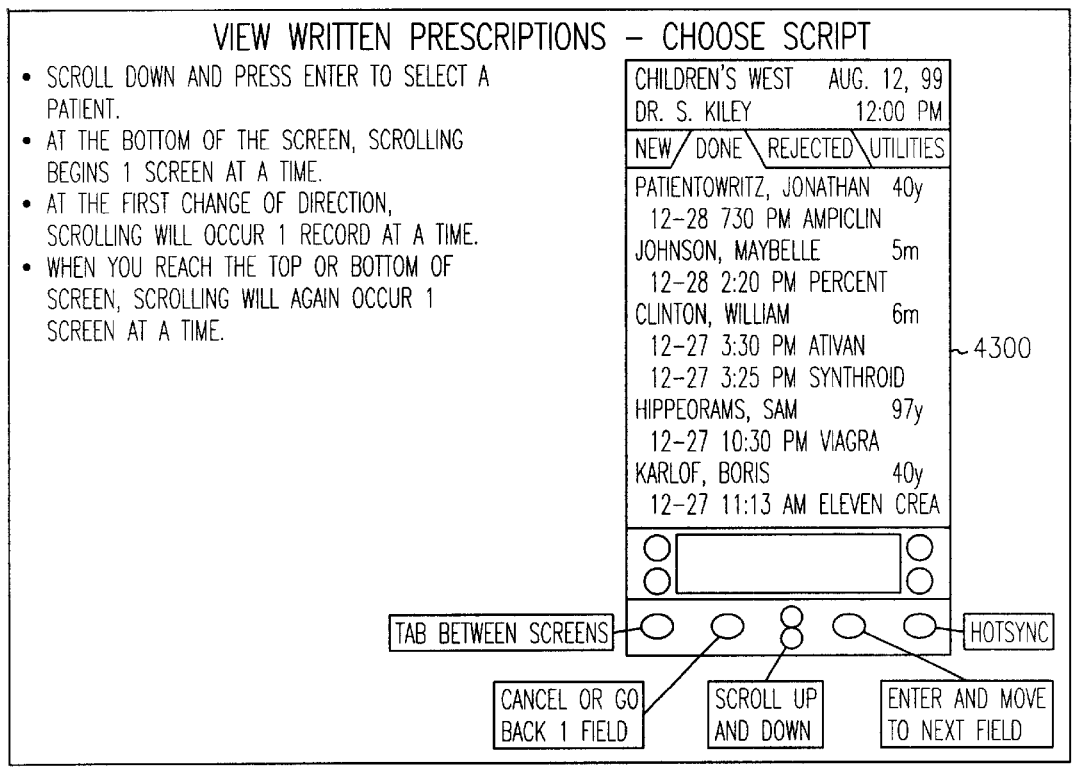
Figure 26E:
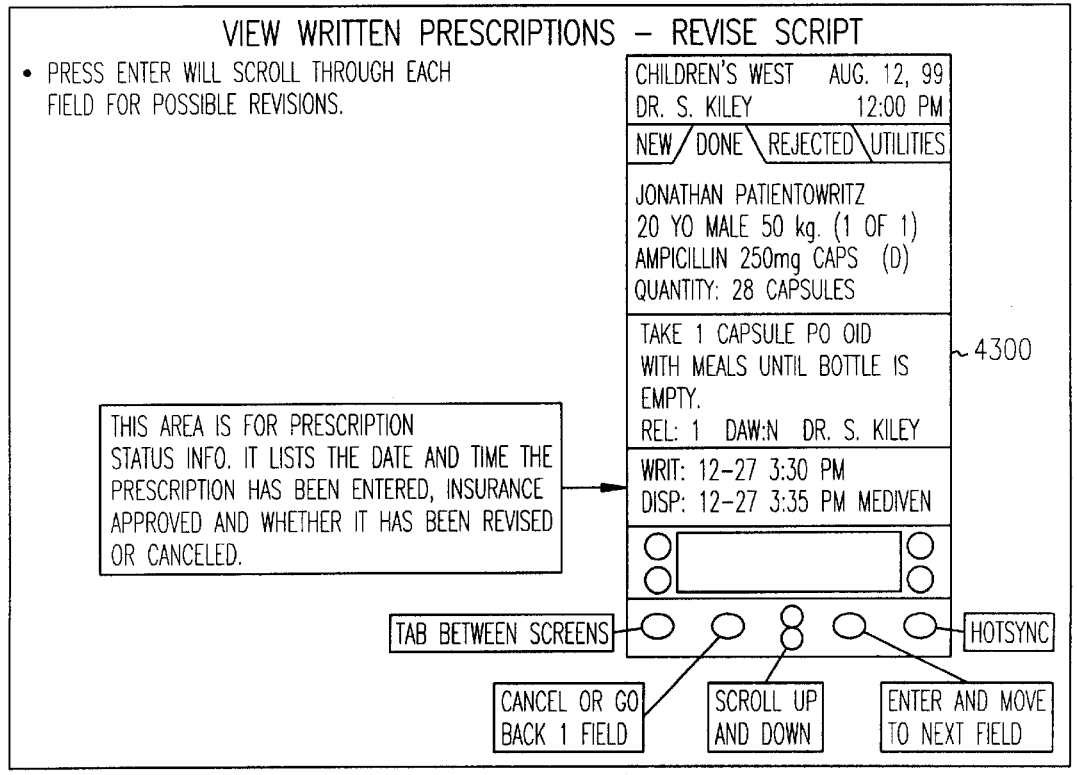
Figure 27B:
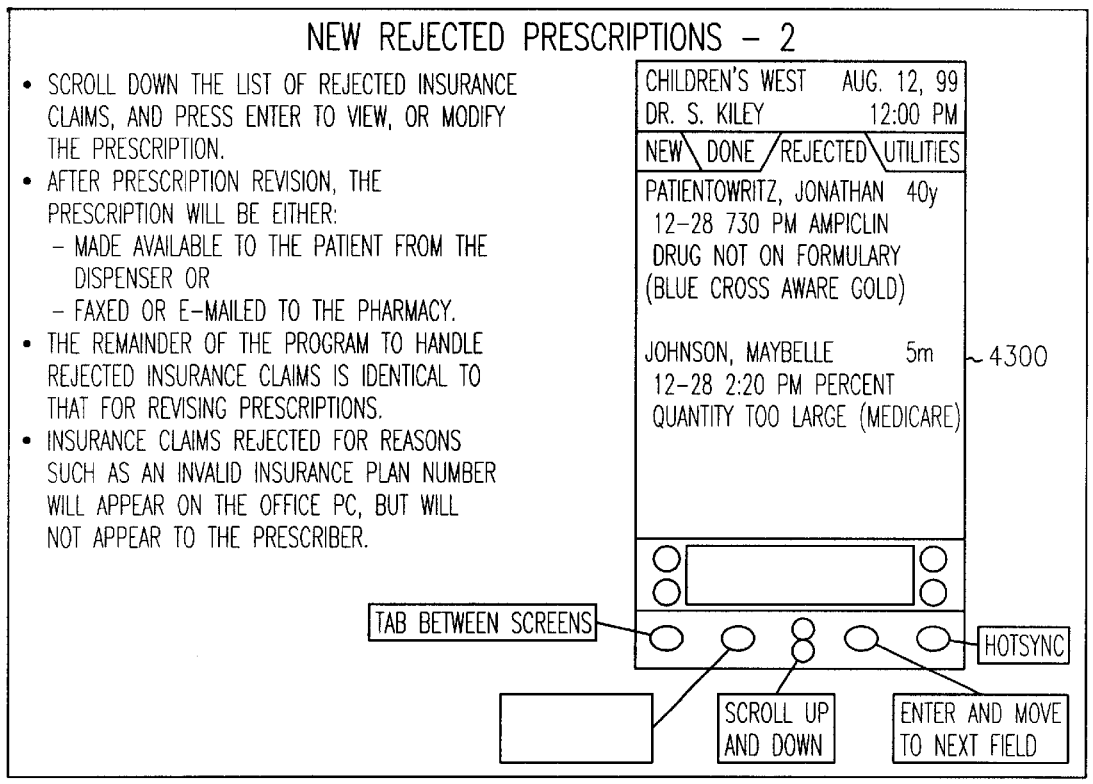
Figure 27C:
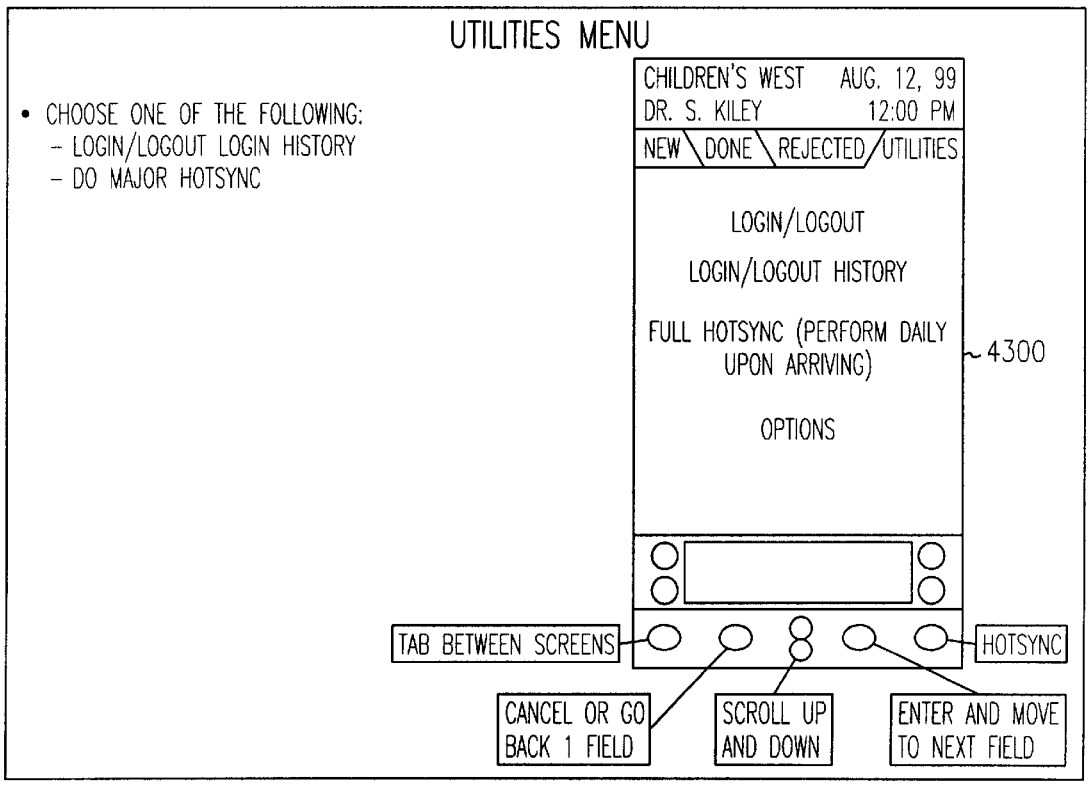
Figure 27D:
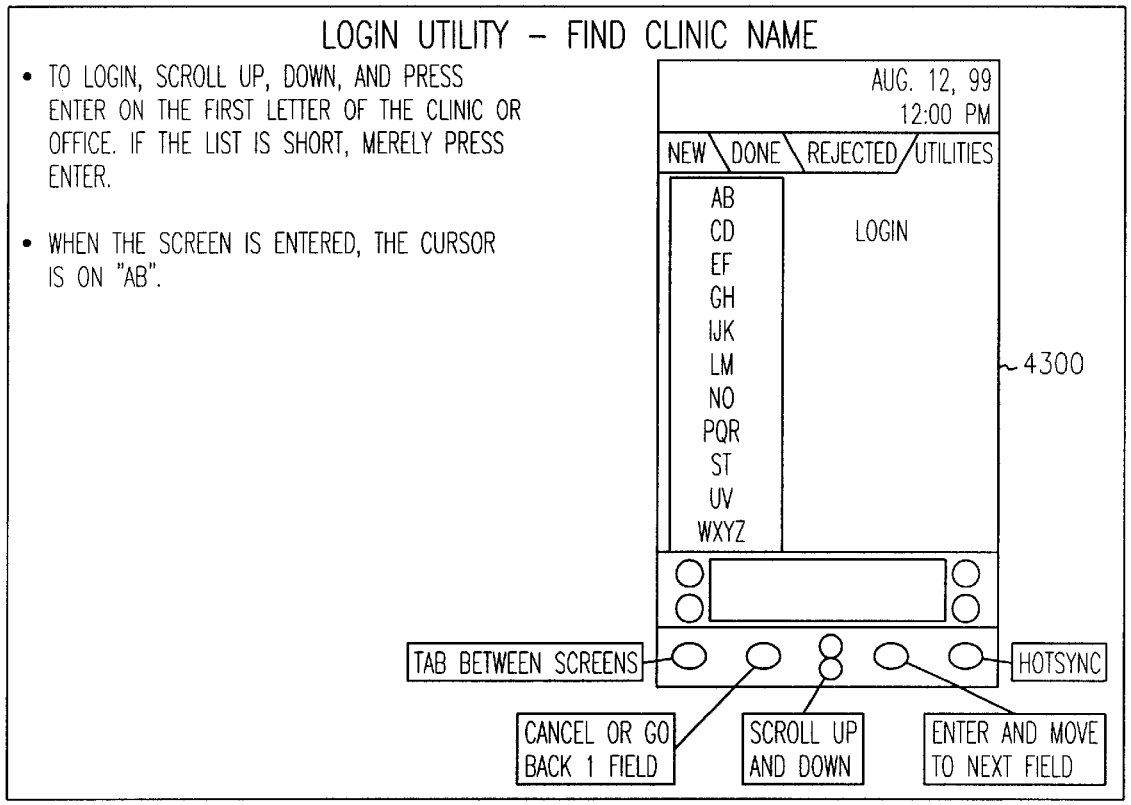
Figure 27E:
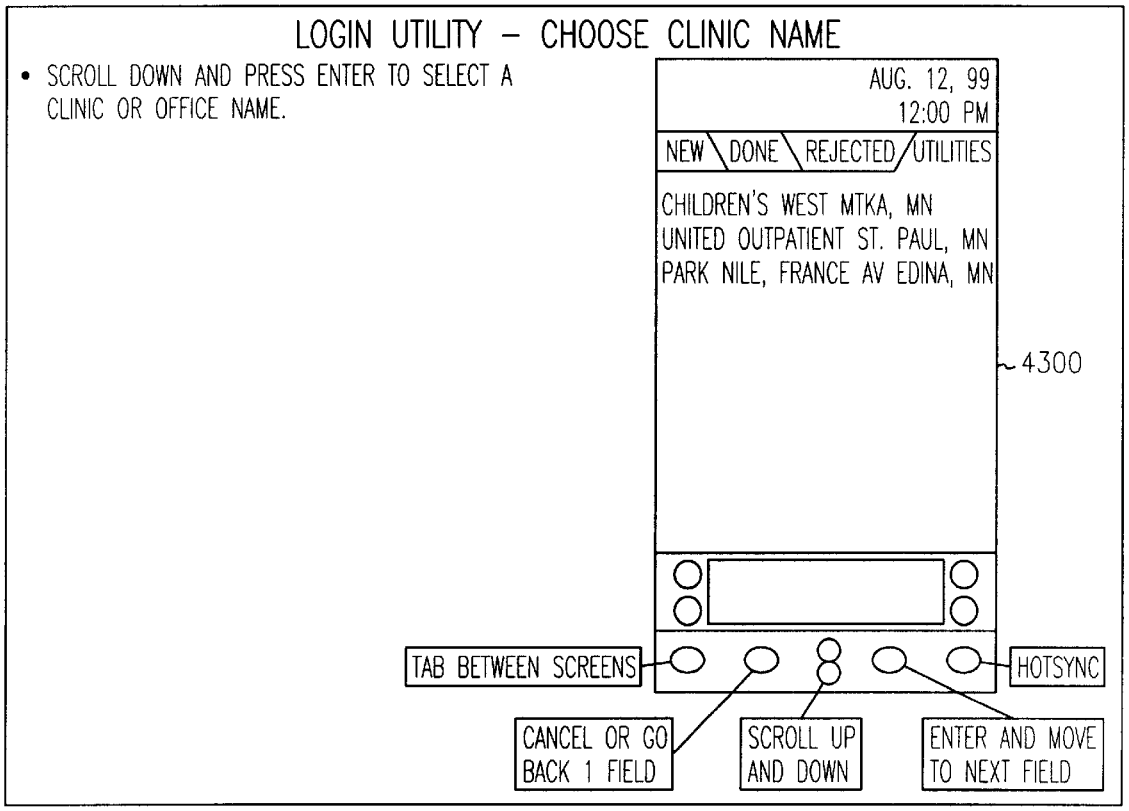
Figure 27F:
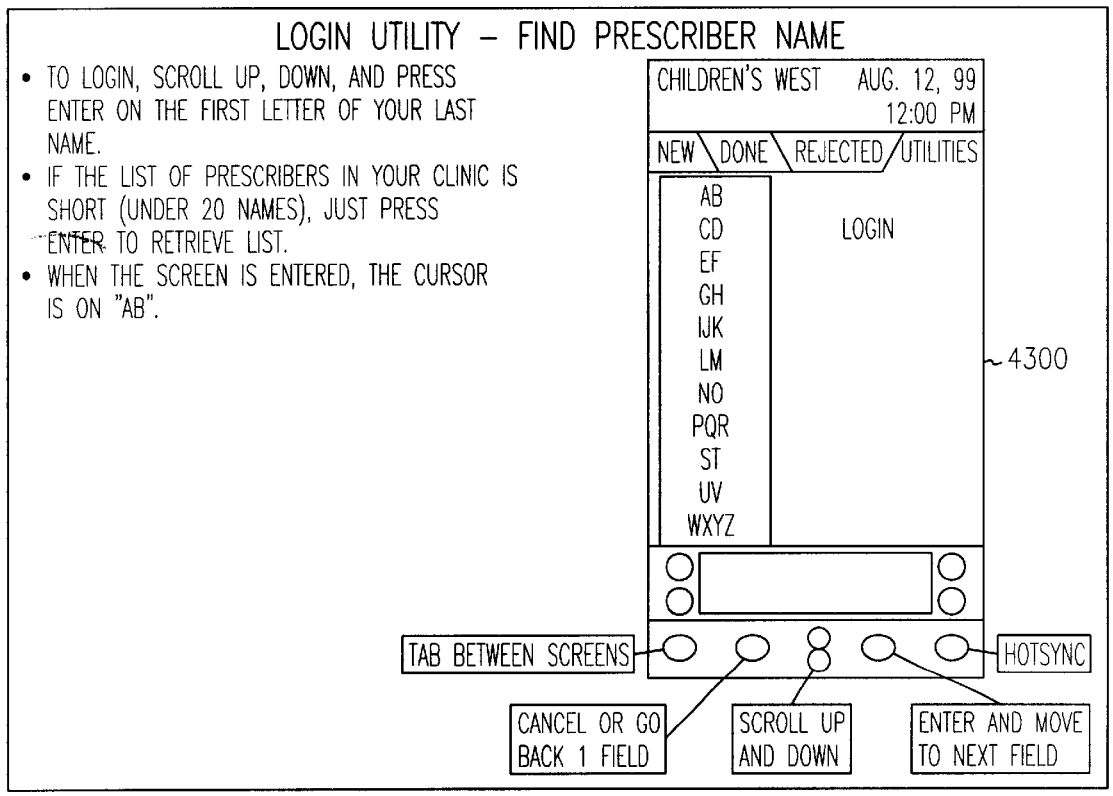
Figure 28A:
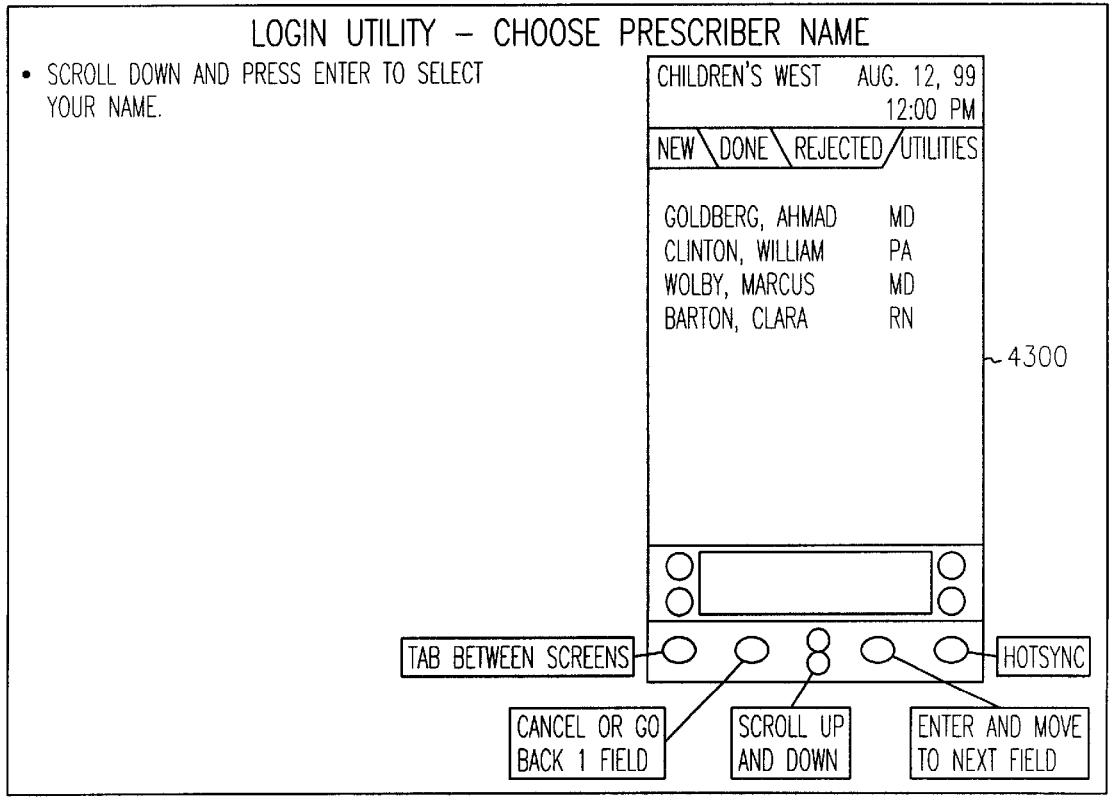
Figure 28B:
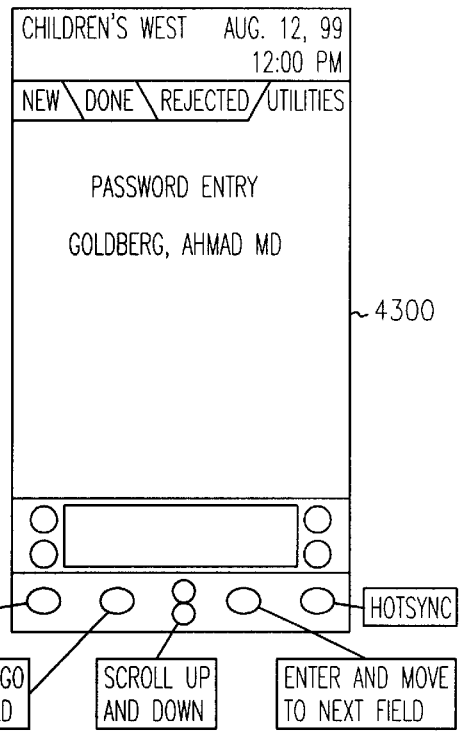
Figure 28C:
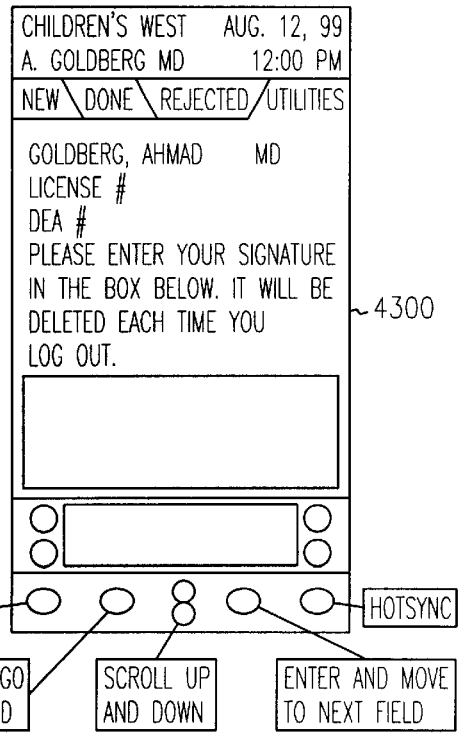

FIG. 23B shows an exemplary screen for choosing a patient for a new prescription. The user scrolls through a patient list using scroll button 4330 to select a patient name. At either the top or the bottom of the screen scrolling begins one screen at a time. At the first change of direction, scrolling begins one patient name at a time. A new patient's name may be entered by pressing enter button 4340 on the dotted line. Optionally, the program defaults to pop up a window to enter the weight if the weight is not shown.

FIG. 25C shows an exemplary screen for picking a quantity for a new prescription. The user uses scroll button 4330 to scroll down to pick a quantity from the list of quantities. Optionally, the quantities are listed in the order of those most commonly written. The list includes a designation, such as a "D" after those quantities available in the remote dispenser. The cursor automatically highlights the closest larger quantity available based on the dosage and length of time to take the medication entered by the user. Optionally, the user may highlight a different quantity or enter a new quantity by pressing the enter key when the dotted line is highlighted.

FIG. 25F shows a screen for choosing how to dispense the prescription. The user may choose between having a written prescription printed out at the dispenser in the waiting room, have the prescription drugs dispensed at the remote dispenser, automatically fax or e-mail the prescription to the patient's pharmacy, or completely cancel the prescription.

CONCLUSION

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

I claim:

1. A method of dispensing therapeutic products to a patient, comprising:
    providing a dispenser containing an inventory of the therapeutic products, the dispenser located in a health care facility;
    a prescriber in the health care facility transmitting a proposed prescription to a server;
    the server adjudicating the proposed prescription into an adjudicated prescription;
    authorizing dispensing of at least a portion of the adjudicated prescription out of the inventory in the dispenser if the adjudicated prescription includes at least one therapeutic product available in the inventory of the dispenser;
    a person in the health care facility providing to the patient an authorization code unique to the combination of patient, adjudicated prescription, and available therapeutic product, wherein the person is not a licensed pharmacist;
    receiving from the patient at the dispenser the authorization code;
    conducting with the patient at the dispenser a financial transaction with respect to the available therapeutic product; and
    providing the available therapeutic product to the patient as an outcome of the financial transaction.

2. A method of dispensing therapeutic products to a patient, comprising:
    providing a dispenser containing an inventory of the therapeutic products;
    a prescriber in a health care facility transmitting a proposed prescription to a server;
    the server adjudicating the proposed prescription into an adjudicated prescription;
    authorizing dispensing of at least a portion of the adjudicated prescription out of the inventory in the dispenser if the adjudicated prescription includes at least one therapeutic product available in the inventory of the dispenser;
    a person in the health care facility providing to the patient an authorization code unique to the combination of patient, adjudicated prescription, and available therapeutic product, wherein the person is not a licensed pharmacist;
    receiving from the patient at the dispenser the authorization code;
    conducting with the patient at the dispenser a financial transaction with respect to the available therapeutic product; and
    providing the available therapeutic product to the patient as an outcome of the financial transaction.

* * * * *